(12) United States Patent
Ibrahim et al.

(10) Patent No.: US 9,994,567 B2
(45) Date of Patent: Jun. 12, 2018

(54) SYNTHESIS OF HETEROCYCLIC COMPOUNDS

(71) Applicant: Plexxikon Inc., Berkeley, CA (US)

(72) Inventors: Prabha N. Ibrahim, Mountain View, CA (US); Jack Lin, Hercules, CA (US); Wayne Spevak, Berkeley, CA (US); Jiazhong Zhang, Foster City, CA (US)

(73) Assignee: Plexxikon Inc., Berkeley, CA (US)

( * ) Notice: Subject to any disclaimer, the term of this patent is extended or adjusted under 35 U.S.C. 154(b) by 0 days. days.

(21) Appl. No.: 15/705,097

(22) Filed: Sep. 14, 2017

(65) Prior Publication Data

US 2018/0002332 A1     Jan. 4, 2018

Related U.S. Application Data

(63) Continuation of application No. 15/161,103, filed on May 20, 2016, now Pat. No. 9,776,998.

(60) Provisional application No. 62/165,808, filed on May 22, 2015.

(51) Int. Cl.
*C07D 471/04* (2006.01)
*C07D 403/04* (2006.01)

(52) U.S. Cl.
CPC ......... *C07D 471/04* (2013.01); *C07D 403/04* (2013.01)

(58) Field of Classification Search
CPC ........................... C07D 403/04; C07D 471/04
USPC ...................................................... 544/333
See application file for complete search history.

(56) References Cited

U.S. PATENT DOCUMENTS

| | | |
|---|---|---|
| 9,260,437 B2 | 2/2016 | Ibrahim et al. |
| 9,358,235 B2 | 6/2016 | Bollag et al. |
| 9,440,969 B2 | 9/2016 | Ibrahim et al. |
| 9,447,089 B2 | 9/2016 | Desai et al. |
| 9,469,640 B2 | 10/2016 | Wu et al. |
| 9,487,515 B2 | 11/2016 | Zhang et al. |
| 9,550,768 B2 | 1/2017 | Zhang et al. |
| 9,617,267 B2 | 4/2017 | Ibrahim et al. |
| 9,624,213 B2 | 4/2017 | Ibrahim et al. |
| 9,663,517 B2 | 5/2017 | Desai et al. |
| 9,676,748 B2 | 6/2017 | Wu et al. |
| 9,682,981 B2 | 6/2017 | Zhang et al. |
| 9,695,169 B2 | 7/2017 | Ibrahim |
| 9,718,847 B2 | 8/2017 | Zhang et al. |
| 9,730,918 B2 | 8/2017 | Bollag et al. |
| 9,771,369 B2 | 9/2017 | Lin et al. |
| 2014/0357612 A1 | 12/2014 | Zhang et al. |
| 2016/0068528 A1 | 3/2016 | Zhang et al. |
| 2016/0075712 A1 | 3/2016 | Shi et al. |
| 2016/0176865 A1 | 6/2016 | Ibrahim et al. |
| 2016/0326162 A1 | 11/2016 | Lin et al. |
| 2016/0326168 A1 | 11/2016 | Ibrahim et al. |
| 2016/0326169 A1 | 11/2016 | Ibrahim et al. |
| 2016/0339025 A1 | 11/2016 | Ibrahim et al. |
| 2016/0340357 A1 | 11/2016 | Ibrahim et al. |
| 2017/0029413 A1 | 2/2017 | Holladay et al. |
| 2017/0056382 A1 | 3/2017 | Wu et al. |
| 2017/0081326 A1 | 3/2017 | Ibrahim et al. |
| 2017/0157120 A1 | 6/2017 | Ibrahim et al. |
| 2017/0158690 A1 | 6/2017 | Wu et al. |
| 2017/0267660 A1 | 9/2017 | Lin et al. |
| 2017/0283423 A1 | 10/2017 | Zhang et al. |
| 2017/0319559 A1 | 11/2017 | Wu et al. |
| 2017/0320899 A1 | 11/2017 | Zhang et al. |
| 2017/0334909 A1 | 11/2017 | Ibrahim et al. |
| 2017/0349572 A1 | 12/2017 | Wu et al. |
| 2017/0362231 A1 | 12/2017 | Ibrahim et al. |

FOREIGN PATENT DOCUMENTS

| | | |
|---|---|---|
| WO | WO-2012/109075 | 8/2012 |
| WO | WO-2013/181415 | 12/2013 |

OTHER PUBLICATIONS

U.S. Appl. No. 15/288,558, filed Oct. 7, 2016, Zhang et al.
U.S. Appl. No. 15/460,095, filed Mar. 15, 2017, Lin et al.
U.S. Appl. No. 15/605,856, filed May 25, 2017, Ibrahim et al.
U.S. Appl. No. 15/606,682, filed May 26, 2017, Desai et al.
U.S. Appl. No. 15/620,396, filed Jun. 12, 2017, Wu et al.
U.S. Appl. No. 15/627,223, filed Jun. 19, 2017, Zhang et al.
U.S. Appl. No. 15/654,538, filed Jul. 19, 2017, Zhang et al.
U.S. Appl. No. 15/656,990, filed Jul. 21, 2017, Wu et al.
U.S. Appl. No. 15/665,804, filed Aug. 1, 2017, Ibrahim et al.
U.S. Appl. No. 15/669,353, filed Aug. 4, 2017, Bollag et al.
Hulikal, Deuterium Labeled Compounds in Drug Discovery Process, Abstract, 2010.
International Search Report and Written Opinion for International Application No. PCT/US2016/033614 dated Jul. 4, 2016, 10 pages.
U.S. Appl. No. 15/713,502, filed Sep. 22, 2017, Zhang et al.
U.S. Appl. No. 15/725,197, filed Oct. 4, 2017, Ibrahim et al.
U.S. Appl. No. 15/814,179, filed Nov. 15, 2017, Zhang et al.
U.S. Appl. No. 15/838,268, filed Dec. 11, 2017, Zhang et al.
U.S. Appl. No. 15/851,639, filed Dec. 21, 2017, Wu et al.
International Preliminary Report on Patentability for International Application No. PCT/US2016/033614 dated Nov. 28, 2017. 6 pages.

*Primary Examiner* — Deepak R Rao
(74) *Attorney, Agent, or Firm* — Sheppard Mullin Richter & Hampton LLP

(57) ABSTRACT

Provided herein are intermediates and processes useful for facile synthesis of compounds of formula (I):

or a pharmaceutically acceptable salt, a solvate, a tautomer, an isomer or a deuterated analog thereof, wherein Q, $P^1$ and $P^2$ are as defined in this disclosure.

7 Claims, No Drawings

SYNTHESIS OF HETEROCYCLIC COMPOUNDS

CROSS-REFERENCE TO RELATED APPLICATIONS

This application is a continuation of U.S. application Ser. No. 15/161,103, filed May 20, 2016, now U.S. Pat. No. 9,776,998, which claims the benefit under 35 U.S.C. § 119(e) to U.S. Provisional Application No. 62/165,808, filed May 22, 2015, which is hereby incorporated by reference in its entirety.

FIELD

The present disclosure relates to heterocyclic compounds, methods for the preparation thereof, and compounds prepared employing same.

BACKGROUND (R)—N-(3-(5-(2-cyclopropylpyrimidin-5-yl)-1H-pyrrolo[2,3-b]pyridine-3-carbonyl)-2,4-difluorophenyl)-3-fluoropyrrolidine-1-sulfonamide is a potent inhibitor of mutated forms of B-raf B, and can be useful for treatment of B-raf mediated diseases, such as metastatic melanoma, thyroid cancers and colorectal cancers. The compound and its synthesis have been described in WO 2012/109075. There remains interest in developing other versatile and facile processes for the efficient preparation of this and other biologically active molecules, especially, on an industrial scale.

SUMMARY

In one embodiment, the present disclosure provides a compound of formula (I):

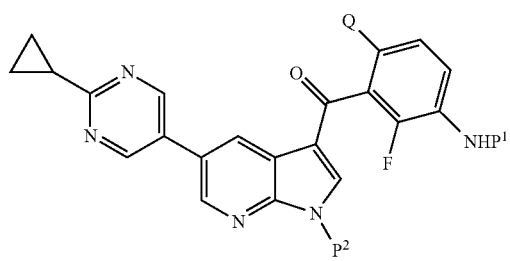

(I)

or a pharmaceutically acceptable salt, a solvate, a tautomer, an isomer or a deuterated analog thereof, wherein:
Q is F or H;
$P^1$ is

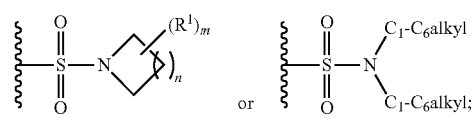

$R^1$ is H or halogen;
n is 0, 1 or 2;
m is 1 or 2;
$P^2$ is —C(O)—$R^3$ or —C(O)—$OR^4$;

$R^3$ is $C_{1-6}$alkyl, aryl, heteroaryl, aryl-$C_{1-2}$alkyl, heteroaryl-$C_{1-2}$alkyl, $C_{3-10}$cycloalkyl, $C_{3-10}$cycloalkyl-$C_{1-2}$alkyl, ethynyl or vinyl, each of which is optionally substituted with 1-3 substituents as described in this disclosure; and $R^4$ is $C_{1-6}$alkyl, aryl, heteroaryl, aryl-$C_{1-2}$alkyl, heteroaryl-$C_{1-2}$alkyl, $C_{3-10}$cycloalkyl, $C_{3-10}$cycloalkyl-$C_{1-2}$alkyl, ethynyl or vinyl, each of which is optionally substituted with 1-3 substituents as described in this disclosure.

In another embodiment, the present disclosure provides a method for preparing a compound of formula (Ia):

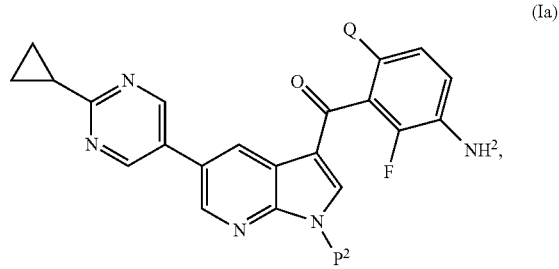

(Ia)

or a pharmaceutically acceptable salt, a solvate, a tautomer, an isomer or a deuterated analog thereof, said method comprising:

contacting a compound of formula (II):

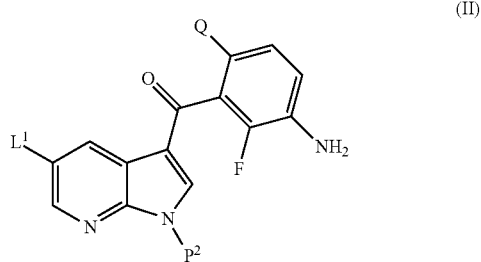

(II)

with an agent of the formula:

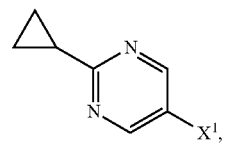

under conditions sufficient to form the compound of formula (Ia), wherein:
$X^1$ is $Sn(Bu)_3$ or $B(OR^5)_2$;
$L^1$ is Br, Cl, I, tosyl-O—, mesyl-O—, trifluoromethanesulfonyl-O—, —C(O)—O—$CF_3$ or —C(O)—O—$CH_3C(O)$O—;
Q is F or H;
$P^2$ is —C(O)—$R^3$ or —C(O)—$OR^4$;
$R^3$ is $C_{1-6}$alkyl, aryl, heteroaryl, aryl-$C_{1-2}$alkyl, heteroaryl-$C_{1-2}$alkyl, $C_{3-10}$cycloalkyl, $C_{3-10}$-cycloalkyl-$C_{1-2}$alkyl, ethynyl or vinyl, each of which is optionally substituted with 1-3 substituents as described in this disclosure;

R⁴ is C₁₋₆alkyl, aryl, heteroaryl, aryl-C₁₋₂alkyl, heteroaryl-C₁₋₂alkyl, C₃₋₁₀cycloalkyl, C₃₋₁₀cycloalkyl-C₁₋₂alkyl, ethynyl or vinyl, each of which is optionally substituted with 1-3 substituents as described in this disclosure; and R⁵ is H or C₁₋₆alkyl which can be optionally substituted with halogen, —OH, or —CN.

In yet another embodiment, the present disclosure provides a method for preparing a compound of formula (I):

(I)

or a pharmaceutically acceptable salt, a solvate, a tautomer, an isomer or a deuterated analog, thereof, said method comprising:

contacting a compound of formula (Ia) with L²-P¹ under conditions sufficient to form the compound of formula (I), wherein:

P¹ is 9-fluorenylmethoxycarbonyl, t-butoxycarbonyl, trimethylsilyl, t-butyldiphenylsilyl, P² is —C(O)—R³ or —C(O)—OR⁴;

R¹ is H or halogen;

R³ is C₁₋₆alkyl, aryl, heteroaryl, aryl-C₁₋₂alkyl, heteroaryl-C₁₋₂alkyl, C₃₋₁₀cycloalkyl, C₃₋₁₀cycloalkyl-C₁₋₂alkyl, ethynyl or vinyl, each of which is optionally substituted with 1-3 substituents as described in this disclosure;

R⁴ is C₃₋₁₀alkyl, aryl, heteroaryl, aryl-C₁₋₂alkyl, heteroaryl-C₁₋₂alkyl, C₃₋₁₀cycloalkyl, C₃₋₁₀cycloalkyl-C₁₋₂alkyl, ethynyl or vinyl, each of which is optionally substituted with 1-3 substituents as described in this disclosure;

Q is H or F;

L¹ is Br, Cl, I, —OSO₂—R¹ or —C(O)—O—R²; wherein R¹ and R² are each independently optionally substituted aryl or optionally substituted C₁₋₆alkyl;

L² is Br, Cl, I, tosyl-O—, mesyl-O—, trifluoromethanesulfonyl-O—, —C(O)—O—CF₃ or —C(O)—O—CH₃;

m is 1 or 2; and n is 1 or 2.

In yet another embodiment, the present disclosure provides a method for preparing a compound of formula (III):

(III)

or a pharmaceutically acceptable salt, a solvate, a tautomer, an isomer or a deuterated analog thereof, said method comprising:

(1) reacting a compound of formula (Ib):

(Ib)

under conditions sufficient to N-deprotect formula (I) and form the compound of formula (III), wherein:

Z is

R¹ is flouro or chloro;

Q is H or fluoro;

n is 0, 1 or 2;

m is 1 or 2;

P² is —C(O)—R³ or —C(O)—OR⁴;

R³ is C₁₋₆alkyl, aryl, heteroaryl, aryl-C₁₋₂alkyl, heteroaryl-C₁₋₂alkyl, C₃₋₁₀cycloalkyl, C₃₋₁₀cycloalkyl-C₁₋₂alkyl, ethynyl or vinyl, each of which is optionally substituted with 1-3 substituents as described in this disclosure; and R⁴ is C₁₋₆alkyl, aryl, heteroaryl, aryl-C₁₋₂alkyl, heteroaryl-C₁₋₂alkyl, C₃₋₁₀cycloalkyl, C₃₋₁₀cycloalkyl-C₁₋₂alkyl, ethynyl or vinyl, each of which is optionally substituted with 1-3 substituents as described in this disclosure.

DETAILED DESCRIPTION

The present disclosure is related to novel synthetic intermediates and processes for the large-scale preparation of compounds that have the following core structure:

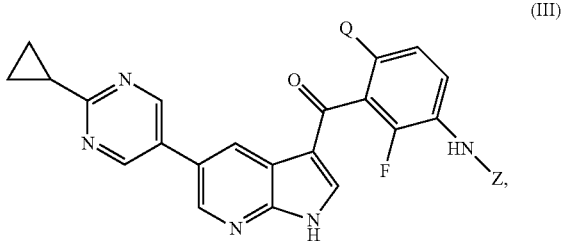

(III)

or a pharmaceutically acceptable salt, a solvate, a tautomer, an isomer or a deuterated analog thereof, wherein:

Z is

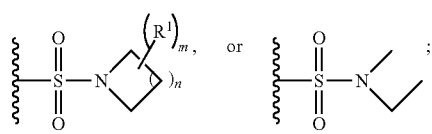

Q is fluoro or chloro;
R₁ is fluoro or chloro;
m is 1 or 2; and
n is 1 or 2.

The wavy lines indicate the points of attachment to the remainder of the structure. For example, the present disclosure provides synthetic methods and intermediates useful for the large scale preparation of (R)—N-(3-(5-(2-cyclopropylpyrimidin-5-yl)-1H-pyrrolo[2,3-b]pyridine-3-carbonyl)-2,4-difluorophenyl)-3-fluoropyrrolidine-1-sulfonamide having the following structure:

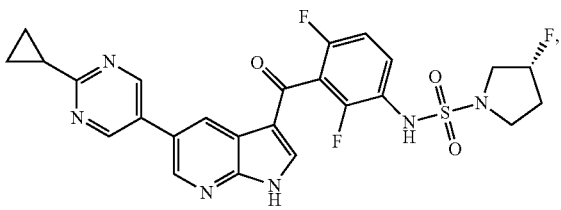 [SMILES: O=C(c1c(F)ccc(NS(=O)(=O)N2CC[C@@H](F)C2)c1F)c1c[nH]c2ncc(-c3cnc(C4CC4)nc3)cc12]

or a pharmaceutically acceptable salt, a solvate, a tautomer, an isomer or a deuterated analog thereof.

Advantageously, the present disclosure provides synthetic intermediates and versatile processes, which allow for high efficiency, low cost and large-scale facile synthesis of biologically active molecules with high purity. The intermediates of the present disclosure can be readily adapted to the facile preparation of various compounds having a fluoro substituent.

Definitions

It is noted here that as used in this specification and the appended claims, the singular forms "a," "an," and "the" include plural reference unless the context clearly dictates otherwise.

"Halogen" or "halo" refers to all halogens, that is, chloro (Cl), fluoro (F), bromo (Br), or iodo (I).

"Hydroxyl" or "hydroxy" refers to the group —OH.

"Thiol" refers to the group —SH.

The term "alkyl", by itself or as part of another substituent, means, unless otherwise stated, a straight or branched chain hydrocarbon, having the number of carbon atoms designated (i.e. $C_{1-6}$ means one to six carbons). Representative alkyl groups include straight and branched chain alkyl groups having 1, 2, 3, 4, 5, 6, 7, 8, 9, 10, 11 or 12 carbon atoms. Further representative alkyl groups include straight and branched chain alkyl groups having 1, 2, 3, 4, 5, 6, 7 or 8 carbon atoms. Examples of alkyl groups include methyl, ethyl, n-propyl, isopropyl, n-butyl, t-butyl, isobutyl, sec-butyl, n-pentyl, n-hexyl, n-heptyl, n-octyl, and the like. For each of the definitions herein (e.g., alkyl, alkoxy, alkylamino, alkylthio, alkylene, haloalkyl, arylalkyl, cycloalkylalkyl, heterocycloalkylalkyl, heteroarylalkyl), when a prefix is not included to indicate the number of carbon atoms in an alkyl portion, the alkyl moiety or portion thereof will have 12 or fewer main chain carbon atoms or 8 or fewer main chain carbon atoms or 6 or fewer main chain carbon atoms. For example, $C_{1-8}$ alkyl refers to a straight or branched hydrocarbon having 1, 2, 3, 4, 5 or 6 carbon atoms and includes, but are not limited to, $C_{1-2}$ alkyl, $C_{1-4}$ alkyl, $C_{2-6}$ alkyl, $C_{2-4}$ alkyl, $C_{1-6}$ alkyl, $C_{2-8}$ alkyl, $C_{1-7}$ alkyl, $C_{2-7}$ alkyl and $C_{3-6}$ alkyl. "Fluoro substituted alkyl" denotes an alkyl group substituted with one or more fluoro atoms, such as perfluoroalkyl, where preferably the lower alkyl is substituted with 1, 2, 3, 4 or 5 fluoro atoms, also 1, 2, or 3 fluoro atoms. While it is understood that substitutions are attached at any available atom to produce a stable compound, when optionally substituted alkyl is an R group of a moiety such as —OR (e.g. alkoxy), —SR (e.g. thioalkyl), —NHR (e.g. alkylamino), —C(O)NHR, and the like, substitution of the alkyl R group is such that substitution of the alkyl carbon bound to any O, S, or N of the moiety (except where N is a heteroaryl ring atom) excludes substituents that would result in any O, S, or N of the substituent (except where N is a heteroaryl ring atom) being bound to the alkyl carbon bound to any O, S, or N of the moiety.

The term "alkylene" by itself or as part of another substituent means a linear or branched saturated divalent hydrocarbon moiety derived from an alkane having the number of carbon atoms indicated in the prefix. For example, (i.e., $C_{1-6}$ means one to six carbons; $C_{1-6}$ alkylene is meant to include methylene, ethylene, propylene, 2-methylpropylene, pentylene, hexylene and the like). $C_{1-4}$ alkylene includes methylene —CH₂—, ethylene —CH₂CH₂—, propylene —CH₂CH₂CH₂—, and isopropylene —CH(CH₃)CH₂—, —CH₂CH(CH₃)—, —CH₂—(CH₂)₂CH₂—, —CH₂—CH(CH₃)CH₂—, —CH₂—C(CH₃)₂—, —CH₂—CH₂CH(CH₃)—. Typically, an alkyl (or alkylene) group will have from 1 to 24 carbon atoms, with those groups having 10 or fewer, 8 or fewer, or 6 or fewer carbon atoms being preferred in the present disclosure. When a prefix is not included to indicate the number of carbon atoms in an alkylene portion, the alkylene moiety or portion thereof will have 12 or fewer main chain carbon atoms or 8 or fewer main chain carbon atoms, 6 or fewer main chain carbon atoms or 4 or fewer main chain carbon atoms.

"Cycloalkylalkyl" refers to an -(alkylene)-cycloalkyl group where alkylene as defined herein has the indicated number of carbon atoms or if unspecified having six or fewer, preferably four or fewer main chain carbon atoms; and cycloalkyl is as defined herein has the indicated number of carbon atoms. $C_{3-8}$cycloalkyl-$C_{1-2}$alkyl means $C_{3-8}$cycloalkyl-$C_{1-2}$alkylene, wherein the cycloalkyl has 3 to 8 ring carbon atoms and the alkylene has 1 or 2 carbon atoms. Exemplary cycloalkylalkyl include, e.g., cyclopropylmethylene, cyclobutylethylene, cyclobutylmethylene, and the like.

"Cycloalkyl" by itself or as part of another substituent, refers to saturated or unsaturated, non-aromatic monocyclic, bicyclic or tricyclic carbon ring systems of 3-10, also 3-8, more preferably 3-6, ring members per ring, such as cyclopropyl, cyclopentyl, cyclohexyl, 1-cyclohexenyl, adamantyl, and the like. Cycloalkyl refers to hydrocarbon rings having the indicated number of ring atoms (e.g., C3-8 cycloalkyl means three to eight ring carbon atoms).

"Haloalkyl" is meant to include alkyl substituted by one to seven halogen atoms. Haloalkyl includes monohaloalkyl and polyhaloalkyl. For example, the term "C1-6 haloalkyl" is meant to include trifluoromethyl, difluoromethyl, 2,2,2-trifluoroethyl, 4-chlorobutyl, 3-bromopropyl, and the like.

"Haloalkoxy" refers to a —O-haloalkyl group, where haloalkyl is as defined herein, e. g., trifluoromethoxy, 2,2,2-trifluoroethoxy, difluoromethoxy, and the like.

"Alkoxy" refers to a —O-alkyl group, where alkyl is as defined herein. "Cycloalkoxy" refers to a —O-cycloalkyl group, where cycloalkyl is as defined herein. "Fluoro substituted alkoxy" denotes alkoxy in which the alkyl is substituted with one or more fluoro atoms, where preferably the alkoxy is substituted with 1, 2, 3, 4 or 5 fluoro atoms, also 1, 2, or 3 fluoro atoms. While it is understood that substitutions on alkoxy are attached at any available atom to produce a stable compound, substitution of alkoxy is such that O, S, or N (except where N is a heteroaryl ring atom), are not bound to the alkyl carbon bound to the alkoxy O. Further, where alkoxy is described as a substituent of another moiety, the alkoxy oxygen is not bound to a carbon atom that is bound to an O, S, or N of the other moiety (except where N is a heteroaryl ring atom), or to an alkene or alkyne carbon of the other moiety.

"Amino" or "amine" denotes the group —NH2.

"Alkylamino" refers to a —NH-alkyl group, where alkyl is as defined herein. Exemplary alkylamino groups include CH3NH—, ethylamino, and the like.

"Dialkylamino" refers to a —N(alkyl)(alkyl) group, where each alkyl is independently as defined herein. Exemplary dialkylamino groups include dimethylamino, diethylamino, ethylmethylamino, and the like.

"Cycloalkylamino" denotes the group —NRddRee, where Rdd and Ree combine with the nitrogen to form a 5-7 membered heterocycloalkyl ring, where the heterocycloalkyl may contain an additional heteroatom within the ring, such as O, N, or S, and may also be further substituted with alkyl, haloalkyl, haloalkoxy, alkoxy, aryl, heteroaryl, arylalkyl, heteroarylalkyl, cycloalkyl, cycloalkylalkyl or R' as defined herein. Alternatively, "cycloalkylamino" refers to a —NH-cycloalkyl group, where cycloalkyl is as defined herein.

"Arylamino" refers to a —NH-aryl group, where aryl is as defined herein. Exemplary arylamino groups include PhNH—, naphthylamino, and the like.

"Heteroarylamino" refers to a —NH-heteroaryl group, where heteroaryl is as defined herein. Exemplary heteroarylamino groups include pyridinyl-NH—, pyrimidinyl-amino, and the like.

"Aryl" by itself or as part of another substituent refers to a monocyclic, bicyclic or polycyclic polyunsaturated aromatic hydrocarbon moiety containing 6 to 14 ring carbon atoms. Non-limiting examples of unsubstituted aryl groups include phenyl, 1-naphthyl, 2-naphthyl and 4-biphenyl. Exemplary aryl group, such as phenyl or naphthyl, which may be optionally fused with a cycloalkyl of preferably 5-7, more preferably 5-6, ring members.

"Arylalkyl" refers to -(alkylene)-aryl, where the alkylene group is as defined herein and has the indicated number of carbon atoms, or if unspecified having six or fewer main chain carbon atoms or four or fewer main chain carbon atoms; and aryl is as defined herein. For example, aryl-C1-2alkyl means aryl-alkylene-, where the alkylene has 1 or 2 carbon atoms. Examples of arylalkyl include benzyl, phenethyl, and the like.

"Heteroaryl" by itself or as part of another substituent refers to a monocyclic aromatic ring structure containing 5 or 6 ring atoms, or a bicyclic aromatic group having 8 to 10 atoms, containing one or more, preferably 1-4, more preferably 1-3, even more preferably 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable compound is produced. Examples of heteroaryl groups include, but are not limited to, pyridinyl, pyridazinyl, pyrazinyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, indolyl, triazinyl, quinoxalinyl, cinnolinyl, phthalaziniyl, benzotriazinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzothienyl, quinolyl, isoquinolyl, indazolyl, pteridinyl and thiadiazolyl. "Nitrogen containing heteroaryl" refers to heteroaryl wherein any heteroatoms are N.

"Heteroarylalkyl" refers to -(alkylene)-heteroaryl, where the alkylene group is as defined herein and has the indicated number of carbon atoms, or if unspecified having six or fewer main chain carbon atoms or four or fewer main chain carbon atoms; and heteroaryl is as defined herein. For example, heteroaryl-C1-2alkyl means heteroaryl-alkylene-, where the alkylene has 1 or 2 carbon atoms. Examples of heteroarylalkyl include 2-pyridylmethyl, 2-thiazolylethyl, and the like.

"Heterocycloalkyl" refers to a saturated or unsaturated non-aromatic cycloalkyl group that contains from one to five heteroatoms selected from N, O, and S, wherein the nitrogen and sulfur atoms are optionally oxidized, and the nitrogen atom(s) are optionally quaternized, the remaining ring atoms being C, where one or two C atoms may optionally be replaced by a carbonyl. The heterocycloalkyl may be a monocyclic, a bicyclic or a polycylic ring system of 3 to 12, preferably 4 to 10 ring atoms, more preferably 5 to 8 ring atoms, even more preferably 4-6 ring atoms in which one to five ring atoms are heteroatoms selected from —N═, —N—, —O—, —S—, —S(O)—, or —S(O)$_2$— and further wherein one or two ring atoms are optionally replaced by a —C(O)— group. The heterocycloalkyl can also be a heterocyclic alkyl ring fused with a cycloalkyl, an aryl or a heteroaryl ring. Non limiting examples of heterocycloalkyl groups include pyrrolidinyl, piperidinyl, imidazolidinyl, pyrazolidinyl, butyrolactam moiety, valerolactam moiety, imidazolidinone moiety, hydantoin, dioxolane moiety, phthalimide moiety, piperidine, 1,4-dioxane moiety, morpholinyl, thiomorpholinyl, thiomorpholinyl-S-oxide, thiomorpholinyl-S,S-oxide, piperazinyl, pyranyl, pyridine moiety, 3-pyrrolinyl, thiopyranyl, pyrone moiety, tetrahydrofuranyl, tetrahydrothiophenyl, quinuclidinyl, and the like. A heterocycloalkyl group can be attached to the remainder of the molecule through a ring carbon or a heteroatom.

"Heterocycloalkylalkyl" refers to -(alkylene)-heterocycloalkyl, where the alkylene group is as defined herein and has the indicated number of carbon atoms, or if unspecified having six or fewer main chain carbon atoms or four or fewer main chain carbon atoms; and heterocycloalkyl is as defined herein. Examples of heterocycloalkylalkyl include 2-pyridylmethyl, 2-thiazolylethyl, and the like.

The substituents for alkyl, alkoxy, haloalkyl, haloalkoxy, cycloalkyl, cycloalkylalkyl, alkylene, vinyl include, but are not limited to, R', halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR', —SR', —OC(O)R', —OC(S)R', —C(O)R', —C(S)R', —C(O)OR', —C(S)OR', —S(O)R', —S(O)$_2$R', —C(O)NHR', —C(S)NHR', —C(O)NR'R", —C(S)NR'R", —S(O)$_2$NHR', —S(O)$_2$NR'R", —C(NH)NHR', —C(NH)NR'R", —NHC(O)R', —NHC(S)R', —NR"C(O)R', —NR'C(S)R", —NHS(O)$_2$R', —NR'S(O)$_2$R", —NHC(O)NHR', —NHC(S)NHR', —NR'C(O)NH$_2$, —NR'C(S)NH$_2$, —NR'C(O)NHR", —NR'C(S)NHR", —NHC(O)NR'R", —NHC(S)NR'R", —NR'C(O)NR"R'", —NR'"C(S)NR'R", —NHS(O)$_2$NHR', —NR'S(O)$_2$NH$_2$, —NR'S(O)$_2$NHR", —NHS(O)$_2$NR'R", —NR'S(O)$_2$NR"R'", —NHR', and —NR'R" in a number ranging from zero to (2m'+1), where m' is the total number of carbon atoms in such group. R', R" and R'" each independently refer to hydrogen, C$_{1-8}$ alkyl, heterocycloalkyl, aryl, heteroaryl, arylalkyl, heteroarylalkyl, aryl substituted with 1-3 halogens, C$_{1-8}$ alkoxy, haloalkyl, haloalkoxy or C$_{1-8}$ thioalkoxy groups, or unsubstituted aryl-C$_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl. R', R" and R'" can be further substituted with R$^{a1}$, halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NH(S)O$_2$NH$_2$, —C(NH)NH$_2$, —OR$^{a1}$, —SR$^{a1}$, —OC(O)R$^{a1}$, —OC(S)R$^{a1}$, —C(O)R$^{a1}$, —C(S)R$^{a1}$, —C(O)OR$^{a1}$, —C(S)OR$^{a1}$, —S(O)R$^{a1}$, —S(O)$_2$R$^{a1}$, —C(O)NHR$^{a1}$, —C(S)NHR$^{a1}$, —C(O)NR$^{a1}$R$^{a2}$, —C(S)NR$^{a1}$R$^{a2}$, —S(O)$_2$NHR$^{a1}$, —S(O)$_2$NR$^{a1}$R$^{a2}$, —C(NH)NHR$^{a1}$, —C(NH)NR$^{a1}$R$^{a2}$, —NHC(O)R$^{a1}$, —NHC(S)R$^{a1}$, —NR$^{a2}$C(O)R$^{a1}$, —NR$^{a1}$C(S)R$^{a2}$, —NHS(O)$_2$R$^{a1}$, —NR$^{a1}$S(O)$_2$R$^{a2}$, —NHC(O)NHR$^{a1}$, —NHC(S)NHR$^{a1}$, —NR$^{a1}$C(O) NH$_2$, —NR$^{a1}$C(S)NH$_2$, —NR$^{a1}$C(O)NHR$^{a2}$, —NR$^{a1}$C(S)NHR$^{a2}$, —NHC(O)NR$^{a1}$R$^{a2}$, —NHC(S) NR$^{a1}$R$^{a2}$, —NR$^{a1}$C(O)NR$^{a2}$R$^{a3}$, —NR$^{a3}$C(S)NR$^{a1}$R$^{a2}$, —NHS(O)$_2$NHR$^{a1}$, —NR$^{a1}$S(O)$_2$NH$_2$, —NR$^{a1}$S(O)$_2$NHR$^{a2}$, —NHS(O)$_2$NR$^{a1}$R$^{a1}$R$^{a2}$, —NR$^{a1}$S(O)$_2$NR$^{a2}$R$^{a3}$, —NHR$^{a1}$, and —NR$^{a1}$R$^{a2}$ in a number ranging from zero to (2n'+1), where n' is the total number of carbon atoms in such group. R$^{a1}$, R$^{a2}$ and R$^{a3}$ each independently refer to hydrogen, C$_{1-8}$ alkyl, heterocycloalkyl, aryl, heteroaryl, arylalkyl, heteroarylalkyl, aryl substituted with 1-3 halogens, C$_{1-8}$ alkoxy, haloalkyl, haloalkoxy or C$_{1-8}$ thioalkoxy groups, or unsubstituted aryl-C$_{1-6}$alkyl groups. R$^{a1}$, R$^{a2}$ and R$^{a3}$ can be further substituted with R$^{b1}$, halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^{b1}$, —SR$^{b1}$, —OC(O)R$^{b1}$, —OC(S)R$^{b1}$, —C(O)R$^{b1}$, —C(S)R$^{b1}$, —C(O)OR$^{b1}$, —C(S)OR$^{b1}$, —S(O)R$^{b1}$, —S(O)$_2$R$^{b1}$, —C(O)NHR$^{b1}$, —C(S)NHR$^{b1}$, —C(O)NR$^{b1}$R$^{b2}$, —C(S)NR$^{b1}$R$^{b2}$, —S(O)$_2$NHR$^{b1}$, —S(O)$_2$NR$^{b1}$R$^{b2}$, —C(NH)NHR$^{b1}$, —C(NH)NR$^{b1}$R$^{b2}$, —NHC(O)R$^{b1}$, —NHC(S)R$^{b1}$, —NR$^{b1}$C(O)R$^{b1}$, —NR$^{b1}$C(S)R$^{b2}$, —NHS(O)$_2$R$^{b1}$, —NR$^{b1}$S(O)$_2$R$^{b2}$, —NHC(O)NHR$^{b2}$, —NHC(S) NHR$^{b1}$, —NR$^{b1}$C(O)NH$_2$, —NR$^{b1}$C(S)NH$_2$, —NR$^{b1}$C(O) NHR$^{b2}$, —NR$^{b1}$C(S)NHR$^{b2}$, —NHC(O)NR$^{b1}$R$^{b1}$, R$^{b2}$, —NHC(S)NR$^{b1}$R$^{b2}$, —NR$^{b1}$C(O)NR$^{b2}$R$^{b3}$, —NR$^{b3}$C(S) NR$^{b1}$R$^{b2}$, —NHS(O)$_2$NHR$^{b1}$, —NR$^{b1}$S(O)$_2$NH$_2$, —NR$^{b1}$S(O)$_2$NHRb$^{b2}$, —NHS(O)$_2$NR$^{b1}$R$^{b2}$, —NR$^{b1}$S(O)$_2$NR$^{b2}$R$^{b3}$, —NHR$^{b1}$, and —NR$^{b1}$R$^{b2}$ in a number ranging from zero to (2p'+1), where p' is the total number of carbon atoms in such group. R$^{b1}$, R$^{b2}$ and R$^{b3}$ each independently refer to hydrogen, C$_{1-8}$ alkyl, heterocycloalkyl, aryl, heteroaryl, arylalkyl, heteroarylalkyl, aryl substituted with 1-3 halogens, C$_{1-8}$ alkoxy, haloalkyl, haloalkoxy or C$_{1-8}$ thioalkoxy groups, or unsubstituted aryl-C$_{1-4}$ alkyl groups.

Substituents for the aryl and heteroaryl groups are varied and are generally selected from: R', halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR', —SR', —OC(O)R', —OC(S)R', —C(O)R', —C(S)R', —C(O)OR', —C(S)OR', —S(O)R', —S(O)$_2$R', —C(O)NHR', —C(S)NHR', —C(O)NR'R", —C(S)NR'R", —S(O)$_2$NHR', —S(O)$_2$NR'R", —C(NH)NHR', —C(NH)NR'R", —NHC(O)R', —NHC(S)R', —NR"C(O)R', —NR'C(S)R", —NHS(O)$_2$R', —NR'S(O)$_2$R", —NHC(O)NHR', —NHC(S)NHR', —NR'C(O)NH$_2$, —NR'C(S)NH$_2$, —NR'C(O)NHR", —NR'C(S)NHR", —NHC(O)NR'R", —NHC(S)NR'R", —NR'C(O)NR"R'", —NR'"C(S)NR'R", —NHS(O)$_2$NHR', —NR'S(O)$_2$NH$_2$, —NR'S(O)$_2$NH R", —NHS(O)$_2$NR'R", —NR'S(O)$_2$NR"R'", —NHR', —NR'R", —N$_3$, perfluoro(C$_{1-4}$)alkoxy, and perfluoro(C$_{1-4}$)alkyl, in a number ranging from zero to the total number of open valences on the aromatic ring system; and where R', R" and R'" are independently selected from hydrogen, haloalkyl, haloalkoxy, C$_{1-8}$ alkyl, C$_{3-6}$ cycloalkyl, cycloalkylalkyl, C$_{2-8}$ alkenyl, C$_{2-8}$ alkynyl, aryl, arylalkyl, heteroaryl, heteroarylalkyl, aryl-C$_{1-4}$ alkyl, and aryloxy-C$_{1-4}$ alkyl. Other suitable substituents include each of the above aryl substituents attached to a ring atom by an alkylene tether of from 1-4 carbon atoms. R', R" and R'" can be further substituted with R$^{a1}$, halogen, —OH, —NH$^2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OC(O)R$^{a1}$, —SR$^{a1}$, —OC(O)R$^{a1}$, —OC(S)R$^{a1}$, —C(O)R$^{a1}$, —C(S)R$^{a1}$, —C(O) OR$^{a1}$, —C(S)OR$^{a1}$, —S(O)R$^{a1}$, —S(O)$_2$R$^{a1}$, —C(O) NHR$^{a1}$, —C(S)NHR$^{a1}$, —C(O)NR$^{a1}$R$^{a2}$, —C(S)NR$^{a1}$R$^{a2}$, —S(O)$_2$NHR$^{a1}$, —S(O)$_2$NR$^{a1}$R$^{a2}$, —C(NH)NHR$^{a1}$, —C(NH)NR$^{a1}$R$^{a2}$, —NHC(O)R$^{a1}$, —NHC(S)R$^{a1}$, —NR$^{a2}$C(O)R$^{a1}$, —NR$^{a1}$C(S)R$^{a2}$, —NHS(O)$_2$R$^{a1}$, —NR$^{a1}$S(O)$_2$R$^{a2}$, —NHC(O)NHR$^{a1}$, —NHC(S)NHR$^{a1}$, —NR$^{a1}$C(O)NH$_2$, —NR$^{a1}$C(S)NH$_2$, —NR$^{a1}$C(O)NHR$^{a2}$, —NR$^{a1}$C(S)NHR$^{a2}$, —NHC(O)NR$^{a1}$R$^{a2}$, —NHC(S) NR$^{a1}$R$^{a2}$, —NR$^{a1}$(O)NR$^{a2}$R$^{a3}$, —NR$^{a3}$C(S)NR$^{a1}$R$^{a2}$, —NHS(O)$_2$NHR$^{a1}$, —NR$^{a1}$S(O)$_2$NH$_2$, —NR$^{a1}$S(O)$_2$NHR$^{a2}$, —NHS(O)$_2$NR$^{a1}$R$^{a2}$, —NR$^{a1}$S(O)$_2$NR$^{a2}$R$^{a3}$, —NHR$^{a1}$, —NR$^{a1}$R$^{a2}$, —N$_3$, perfluoro(C$_1$-C$_4$)alkoxy, and perfluoro(C$_1$-C$_4$)alkyl, in a number ranging from zero to the total number of open valences on the aromatic ring system; and where R$^{a1}$, R$^{a2}$ and R$^{a3}$ are each independently selected from hydrogen, haloalkyl, haloalkoxy, C$_{1-8}$alkyl, C$_{3-6}$ cycloalkyl, cycloalkylalkyl, C$_{2-8}$ alkenyl, C$_{2-8}$ alkynyl, aryl, arylalkyl, heteroaryl, heteroarylalkyl, aryl-C$_{1-4}$ alkyl, or aryloxy-C$_{1-4}$ alkyl. Other suitable substituents include each of the above aryl substituents attached to a ring atom by an alkylene tether of from 1-4 carbon atoms.

When two substituents are present on adjacent atoms of a substituted aryl or a substituted heteroaryl ring, such substituents may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, when two substituents are present on adjacent atoms of a substituted aryl or a substituted heteroaryl ring, such substituents may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, when two substituents are present on adjacent atoms of a substituted aryl or a substituted heteroaryl ring, such substituents may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted C$_{1-6}$ alkyl.

"Protecting group" refers to a grouping of atoms that when attached to a reactive group in a molecule masks, reduces or prevents that reactivity. Examples of protecting groups can be found in T. W. Greene and P. G. Wuts, PROTECTIVE GROUPS IN ORGANIC CHEMISTRY, (Wiley, 4th ed. 2006), Beaucage and Iyer, *Tetrahedron* 48:2223-2311 (1992), and Harrison and Harrison et al., COMPENDIUM OF SYNTHETIC ORGANIC METHODS, Vols. 1-8 (John Wiley and Sons. 1971-1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), tri-isopropylsilyl (TIPS), phenylsulphonyl and the like (see also, Boyle, A. L. (Editor), carbamates, amides, N-sulfonyl derivatives, groups of formula —C(O)OR, wherein R is, for example, methyl, ethyl, t-butyl, benzyl, phenylethyl, CH$_2$=CHCH$_2$—, and the like, groups of the formula —C(O)R', wherein R' is, for example, methyl, phenyl, trifluoromethyl, and the like, groups of the formula —SO$_2$R", wherein R" is, for example, tolyl, phenyl, trifluoromethyl, 2,2,5,7,8-pentamethylchroman-6-yl, 2,3,6-trimethyl-4-methoxyphenyl, and the like, and silanyl containing groups, such as 2-trimethylsilylethoxymethyl, t-butyldimethylsilyl, triisopropylsilyl, and the like, CURRENT PROTOCOLS IN NUCLEIC ACID CHEMISTRY, John Wiley and Sons, New York, Volume 1, 2000).

The term "Labile protecting group" refers to those protecting groups that are removable under mild conditions that do not significantly impact other protecting groups or the remainder of the molecule.

The term "Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

Compounds

In one embodiment, the present disclosure provides a compound of formula (I):

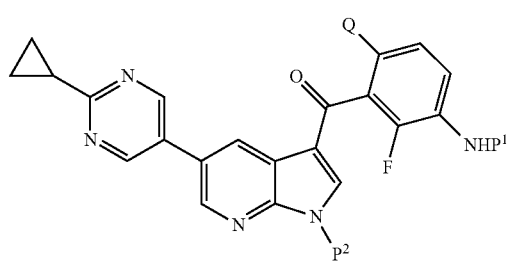

(I)

or a pharmaceutically acceptable salt, a solvate, a tautomer, an isomer or a deuterated analog thereof, wherein the substituents P$^1$, P$^2$ and Q are as defined in this disclosure. In another embodiment of Formula (I), P$^1$ is H.

In another embodiment of Formula (I), P$^1$ is

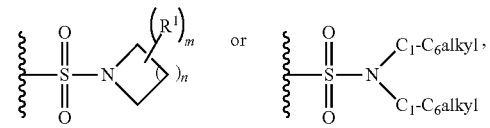

wherein R$^1$, n, and m are as defined in this disclosure.

In another embodiment of Formula (I), P$^1$ is

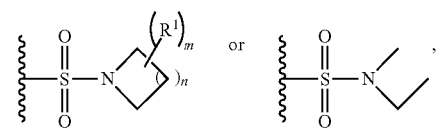

wherein R$^1$, n, and m are as defined in this disclosure.

In another embodiment of Formula (I), P$^1$ is

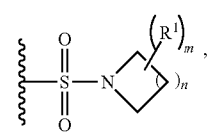

wherein R$^1$, n, and m are as defined in this disclosure.

In another embodiment of Formula (I), P$^1$ is

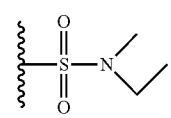

The compounds of formula (I) are useful intermediates for the synthesis of various biologically active molecules, for example, compounds of formula (III):

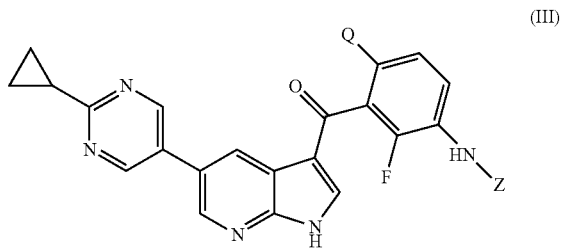

(III)

or a pharmaceutically acceptable salt, a solvate, a tautomer, an isomer or a deuterated analog thereof, wherein Z and Q are as defined in this disclosure.

In other embodiments of this disclosure, Q is F. In other embodiments of this disclosure, Z is

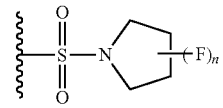

wherein n is 0, 1 or 2.

In other embodiments of this disclosure, Z is

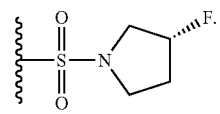

In other embodiments of this disclosure, Z is

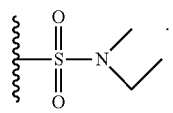

In certain embodiments of compounds of formula (I), $P^1$ can be selectively added or removed in the presence of the $P^2$ group. Selective cleavage of $P^1$ can be accomplished by adjusting the reaction conditions, such as temperature, pH, reaction time and so forth. In some embodiments, In other embodiments of formula (I), $P^1$ is a pyrrolidine sulfonyl optionally substituted with 1-3 halo. In other embodiments of formula (I), $P^1$ is a pyrrolidine sulfonyl optionally substituted with 1-3 fluoro. In other embodiments of formula (I), $P^1$ is a pyrrolidine sulfonyl substituted with 2 fluoro groups. In other embodiments of formula (I), $P^1$ is a pyrrolidine sulfonyl substituted with 1 fluoro group. In other embodiments of formula (I), $P^1$ is an unsubstituted pyrrolidine sulfonyl group.

In certain embodiments of compounds of formula (I), (Ia) or (II), $P^2$ is an amino protecting group, which is capable of forming a carbamate or an amide linkage with the amino group to which it is attached. In some embodiments, $P^2$ is an amino protecting group selected from $R^3$—C(O)— or $R^4O$—C(O)—, wherein $R^3$ and $R^4$ are each independently selected from $C_{1-6}$alkyl, aryl, heteroaryl, aryl-$C_{1-2}$alkyl, heteroaryl-$C_{1-2}$alkyl, $C_{3-10}$cycloalkyl, $C_{3-10}$cycloalkyl-$C_{1-2}$alkyl, ethynyl or vinyl, each of which is optionally substituted. In certain instances, $R^3$ and $R^4$ are each independently selected from $C_{1-6}$ alkyl, aryl, heteroaryl, aryl-$C_{1-2}$alkyl, heteroaryl-$C_{1-2}$alkyl, $C_{3-10}$cycloalkyl, $C_{3-10}$cycloalkyl-$C_{1-2}$alkyl, ethynyl or vinyl, each of which is optionally substituted with 1-3 $R^a$ groups independently selected from halogen, $C_{1-6}$alkyl, $C_{1-6}$haloalkyl, $C_{1-6}$haloalkoxy, fluoro substituted $C_{1-6}$alkyl, fluoro substituted $C_{1-6}$alkoxy, aryl, heteroaryl, $C_{1-6}$alkoxy, —CN, —$NO_2$, —OH, $C_{1-6}$alkyl-OC(O)—, $C_{1-6}$alkyl-C(O)O— or —$SiMe_3$, wherein the aliphatic or aromatic portion of $R^a$ is further optionally substituted with from 1-3 $R^b$ groups independently selected from halogen, $C_{1-6}$alkyl, $C_{1-6}$alkoxy, —CN, —$NO_2$ or —OH. In other instances, $R^3$ and $R^4$ are each independently methyl, ethyl, phenyl, 2,2,2-trichloroethyl, $(CH_3)_2CHC\equiv C$—, 2-trimethylsilylethyl, 1-methyl-1-phenylethyl, cyclobutyl, cyclopropyl, allyl, vinyl, 1-adamantyl, benzyl or diphenylmethyl, each of which is optionally substituted with from 1-3 $R^a$ groups. In some embodiments, $R^a$ is F, Cl, Br, I, —$CH_3$, Phenyl, t-butyl, MeO—, —$NO_2$, —CN, —$CF_3$, $CF_3O$—, —OH or —CH=$CH_2$. In one embodiment, $P^2$ is 2,6-dichlorophenylcarbonyl. In another embodiment, $P^2$ is 2,5-dichlorophenylcarbonyl, 2,3-dichlorophenylcarbonyl or 2,4-dichlorophenylcarbonyl. In certain embodiments, $P^2$ is phenylcarbonyl optionally substituted with from 1-2 groups independently selected from F, Cl, Br, CN or $NO_2$. In some embodiments of compounds of formula (I), $P^2$ is H, and $P^1$ and Q are as defined in any of the embodiments described herein.

In some embodiments of compounds of formula (II), $L^1$ is Br, Cl, I, tosyl-O—, mesyl-O—, trifluoromethanesulfonyl-O—, $R^1$—$SO_2$— or $R^2C(O)O$, wherein $R^1$ and $R^2$ are each independently selected from aryl, aryl-$C_{1-4}$alkyl or $C_{1-6}$alkyl, each of which is optionally substituted with from 1-3 $R^c$ substituents selected from halogen, —CH=$CH_2$, —CN, —OH, —$NH_2$, —$NO_2$, —C(O)OH, —C(O)$NH_2$, —S(O)$_2NH_2$, —NHC(O)$NH_2$, —NHC(S)$NH_2$, —NHS(O)$_2NH_2$, —C(NH)$NH_2$, —$OR^d$, —$SR^d$, —OC(O)$R^d$, —C(O)$R^d$, —C(O)$OR^d$, —C(S)$OR^d$, —S(O)$R^d$, —S(O)$_2R^d$, —C(O)$NHR^d$, —C(O)$NR^dR^d$, —S(O)$_2NHR^d$, —S(O)$_2NR_dR^d$, —C(NH)$NHR^d$, —C(NH)$NR^dR^d$, —NHC(O)$R^d$, —$NR^dC(O)R^d$, —NHS(O)$_2R^d$, —$NR^dS(O)_2R^d$, —NHC(O)$NHR^d$, —$NHR^d$ or —$NR^dR^d$, wherein each $R^d$ is independently selected from $C_{1-6}$alkyl or aryl. In some instances, $R^d$ is —$CH_3$, ethyl or phenyl. In some embodiments of formula (II), $L^1$ is Br, Cl, I, tosyl-O—, mesyl-O—, trifluoromethanesulfonyl-O—, $CF_3C(O)O$— or $CH_3C(O)O$—. In another embodiment of formula (II), $L^1$ is Br or Cl, and $P^2$ and Q are as defined in any of the embodiments described herein.

In another embodiment of formula (I), $P^1$ is H; and Q is F. In another embodiment of formula (I), $P^1$ and Q are H. In another embodiment of formula (I), $P^1$ is H; and Q is F. In another embodiment of formula (I), $P^1$ is H; and $P^2$ is 2,6-dichlorophenylcarbonyl. In another embodiment of formula (I), $P^1$ is 3-R-fluoropyrrolidine sulfonyl, 3-S-fluoropyrrolidine sulfonyl or a 3-fluoropyrrolidine sulfonyl. In yet another embodiment of formula (I), $P^1$ is 3-R-fluoropyrrolidine sulfonyl, $P^2$ is 2,6-dichlorophenylcarbonyl, and Q is F.

Methods

Compound of formula (II) can be synthesized by those methods described in published U.S. Publication No. 2014-0094611-A1, which is incorporated herein by reference in its entirety. The compounds of Formula (a), (V), (VI) and (VII) can either be synthesized by those methods described in published U.S. U.S. Publication No. 2014-0094611-A1, or they can be obtained directly from commercial sources, or they can be obtained by modifying commercially available starting materials using techniques known in the art.

In general, compound of formula (II) can be synthesized by reacting a compound of formula (a):

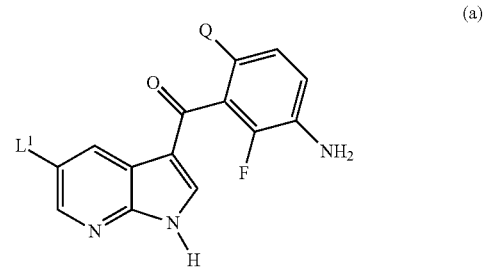

with an agent of the formula: $P^2$-G under conditions sufficient to form the compound of formula (II):

(II)

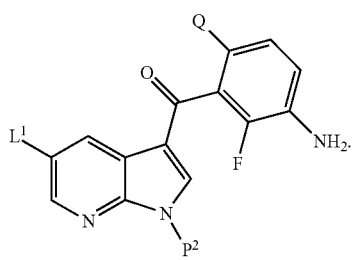

G can be selected from Br, Cl, I, tosyl-O—, mesyl-O—, trifluoromethanesulfonyl-O—, CF$_3$C(O)O— or CH$_3$C(O)O—, or the like.

In another embodiment of Formula (I), (Ia) or (II), P$^2$ is an amino protecting group as described in T. W. Greene and P. G. Wuts, PROTECTIVE GROUPS IN ORGANIC CHEMISTRY, (Wiley, 4th ed. 2006) or as defined in any of the embodiments described herein, and P1 and Q are as defined in any of the embodiments described herein.

In some embodiments, the reactions for preparing compounds of formulas (I) or (Ia) can be carried out in the presence of a base dissolved in an organic solvent. Some preferred bases include dimethylaminopyridine (DMAP), triethylamine (TEA), N,N-diisopropylethylamine (DIPEA) and combinations thereof. DMAP is generally present in a catalytic amount of about 0.05, 0.07, 0.08, 0.1, 0.2, 0.3, 0.4 or 0.5 equivalents. TEA or DIPEA can range from about 1-5 equivalents, for example, 1.0, 2.0, 3.0, 4.0 or 5.0 equivalents. The organic solvents used include, but are not limiting to, tetrahydrofuran (THF), 2-methyl-THF, acetonitrile, dioxane, dichloromethane and benzene. A preferred solvent is 2-methyl-THF. The solvents can be present in various volumes, e.g., 0.5, 1, 2, 3, 4, 5, 6, 7, 8, 9, 10, 11, 12, 13, 14, or 12 volumes.

Compounds of formula (a) can be prepared by contacting a compound of formula (V):

(V)

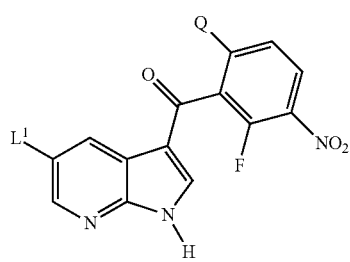

with a reducing agent under conditions sufficient to form the compounds of formula (a). The variables, L$^1$ and Q are as defined in any of the embodiments described herein. In one embodiment, L$^1$ is Br and Q is F. The reducing agent may be, but is not limited to, tin chloride dihydrate (SnCl$_2$.2H$_2$O). Typically, 1-5 equivalents (e.g., 1, 2, 3, 4 or 5 eqs) of the reducing agent are used. The reaction can be carried out at a temperature of about 40-90° C., preferably about 50-70° C., more preferably about 60° C. The solvents for the reaction can be 2-methyl-THF or a mixture of 1:1 ethyl acetate/THF. The volumes of the solvents can be from about 5 to 100 or about 7 to 80. In one embodiment, a compound of formula (V) is treated with 3 or 4 equivalents of SnCl$_2$ in 80 volumes of 1;1 ethyl acetate/THF or 7 volumes of 2-methyl THF at 60° C.

Compounds of formula (V) can be prepared by reacting a compound of formula (VI):

(VI)

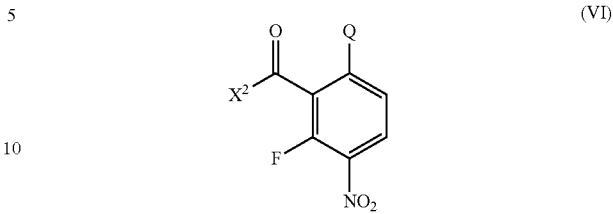

with a compound of formula (VII):

(VII)

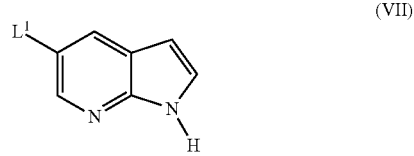

in the presence of a metal halide, such as AlCl$_3$ under conditions sufficient to form the compounds of formula (V). X$^2$ is selected from Br, Cl, I, tosyl-O—, mesyl-O—, trifluoromethanesulfonyl-O—, CF$_3$C(O)O— or CH$_3$C(O)O—. The variables, L$^1$ and Q are as defined in any of the embodiments described herein. In a preferred embodiment, X$^2$ is Br or Cl. In one embodiment, Q is F, L$^1$ is Br and X$^2$ is Cl. The solvents used in the reaction include, but are not limited to, CH$_3$NO$_2$, acetonitrile, dichloromethane, dioxane, dichloroethane, benzene, toluene and combinations thereof. In one embodiment, the solvent is dichloromethane. In one embodiment, the solvent is dioxane. In another embodiment, the solvent is 1,4-dioxane.

In another embodiment, the present disclosure provides a compound of formula (I):

(I)

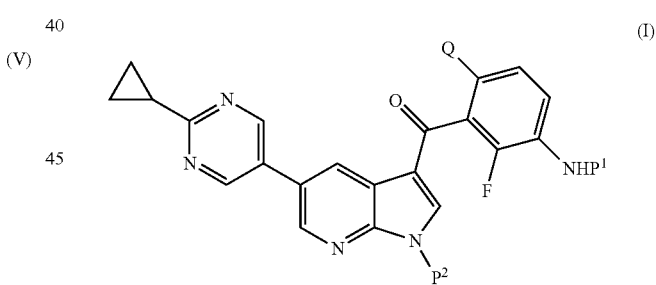

or a pharmaceutically acceptable salt, a solvate, a tautomer, an isomer or a deuterated analog thereof, wherein:

Q is F or H;
P$^1$ is,

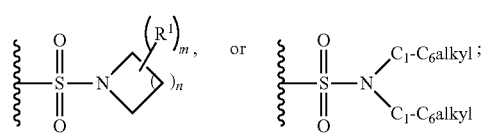

R$^1$ is H or halogen;
n is 0, 1 or 2;
m is 1 or 2;
P$^2$ is —C(O)—R$^3$ or —C(O)—OR$^4$;
R$^3$ is C$_{1-6}$alkyl, aryl, heteroaryl, aryl-C$_{1-2}$alkyl, heteroaryl-C$_{1-2}$alkyl, C$_{3-10}$cycloalkyl, C$_{3-10}$cycloalkyl- C$_{1-2}$alkyl, ethynyl or vinyl, each of which is optionally substituted with 1-3 R$^a$ groups;

R$^4$ is C$_{1-6}$alkyl, aryl, heteroaryl, aryl-C$_{1-2}$alkyl, heteroaryl-C$_{1-2}$alkyl, C$_{3-10}$cycloalkyl, C$_{3-10}$cycloalkyl-C$_{1-2}$alkyl, ethynyl or vinyl, each of which is optionally substituted with 1-3 R$^a$ groups; and each R$^a$ group is independently halogen, C$_{1-6}$alkyl, fluoro substituted C$_{1-6}$alkyl, fluoro substituted C$_{1-6}$alkoxy, aryl, heteroaryl, C$_{1-6}$alkoxy, —CN, —NO$_2$, —OH, —C(O)—O—C$_{1-6}$alkyl, or —SiMe$_3$, wherein the aliphatic or aromatic portion of R$^a$ is further optionally substituted with from 1-3 R$^b$ groups, wherein each R$^b$ group is independently halogen, C$_{1-6}$alkyl, C$_{1-6}$alkoxy, —CN, —NO$_2$ or —OH.

In another embodiment of the compound of formula (I), P$^1$ is —H. In another embodiment of the compound of formula (I), P$^1$ is pyrrolidine sulfonyl optionally substituted with 1-3 halogens. In another embodiment of the compound of formula (I), P$^1$ is pyrrolidine sulfonyl optionally substituted with 1-3 fluoro. In another embodiment of the compound of formula (I), P$^1$ is pyrrolidine sulfonyl optionally substituted with 1-2 fluoro. In another embodiment of the compound of formula (I), P$^1$ is pyrrolidine sulfonyl optionally substituted with 1 fluoro. In another embodiment of the compound of formula (I), P$^1$ is 3-R-fluoropyrrolidine sulfonyl, 3-S-fluoropyrrolidine sulfonyl or a 3-fluoropyrrolidine sulfonyl. In another embodiment of the compound of formula (I), P$^1$ is 3-R-fluoropyrrolidine sulfonyl. In another embodiment of the compound of formula (I), P$^1$ ethyl methyl sulfonyl.

In another embodiment of the compound of formula (I), R$^3$ and R$^4$ are each independently methyl, ethyl, phenyl, 2,2,2-trichloroethyl, (CH$_3$)$_2$CHC≡C—, 2-trimethylsilyl-ethyl, 1-methyl-1-phenylethyl, cyclobutyl, cyclopropyl, allyl, vinyl, 1-adamantyl, benzyl or diphenylmethyl; each of which is optionally substituted with from 1-3 R$^a$ groups, wherein each R$^a$ group is independently F, Cl, Br, I, —CH$_3$, —OCH$_3$, —CH$_2$F, —CHF$_2$, —CF$_3$, phenyl, t-butyl, —NO$_2$, —CN, —OCF$_3$, —CH$_3$, —OCH$_3$, —OH or —CH=CH$_2$. In another embodiment of the compound of formula (I), R$^3$ or R$^4$ is phenyl optionally substituted with 1-2 R$^a$ groups, wherein each R$^a$ group is independently F, Cl, Br, I, —CH$_3$, —CH$_2$F, —CHF$_2$, —CF$_3$, t-butyl, —NO$_2$, —CN, —OCF$_3$, or —OH.

In another embodiment of the compound of formula (I), P$^2$ is phenycarbonyl optionally substituted with 1-3 halogens. In another embodiment of the compound of formula (I), P$^2$ is 2,6-dichlorophenylcarbonyl.

In another embodiment of the compound of formula (I), P$^1$ is H, P$^2$ is 2,6-dichlorophenylcarbonyl, and Q is F. In another embodiment of the compound of formula (I), P$^1$ is 3-R-fluoropyrrolidine sulfonyl, P$^2$ is 2,6-dichlorophenylcarbonyl, and Q is F.

In another embodiment, the present disclosure provides a method for preparing a compound of formula (Ia):

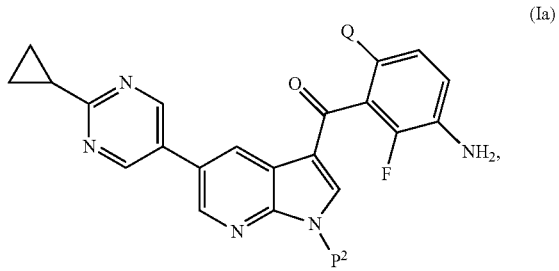

(Ia)

or a pharmaceutically acceptable salt, a solvate, a tautomer, an isomer or a deuterated analog thereof, said method comprising:

contacting a compound of formula (II):

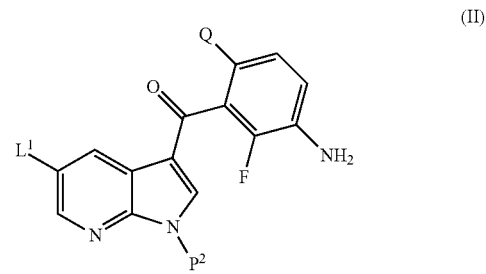

(II)

with an agent of the formula:

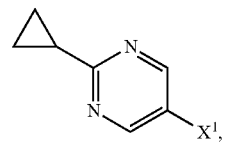

under conditions sufficient to form the compound of formula (Ia), wherein:

X$^1$ is Sn(Bu)$_3$ or B(OR$^5$)$_2$,

L$^1$ is Br, Cl, I, tosyl-O—, mesyl-O—, trifluoromethanesulfonyl-O—, —C(O)—O—CF$_3$ or —C(O)—O—CH$_3$C(O)O—;

Q is F or H;

P$^2$ is —C(O)—R$^3$ or —C(O)—OR$^4$;

R$^3$ is C$_{1-6}$alkyl, aryl, heteroaryl, aryl-C$_{1-2}$alkyl, heteroaryl-C$_{1-2}$alkyl, C$_{3-10}$cycloalkyl, C$_{3-10}$cycloalkyl-C$_{1-2}$alkyl, ethynyl or vinyl, each of which is optionally substituted with 1-3 R$^a$ groups;

R$^4$ is C$_{1-6}$alkyl, aryl, heteroaryl, aryl-C$_{1-2}$alkyl, heteroaryl-C$_{1-2}$alkyl, C$_{3-10}$-cycloalkyl, C$_{3-10}$cycloalkyl-C$_{1-2}$alkyl, ethynyl or vinyl, each of which is optionally substituted with 1-3 R$^a$ groups;

R$^5$ is H or C$_{1-6}$alkyl which can be optionally substituted with halogen, —OH, or —CN; and each R$^a$ group is independently halogen, C$_{1-6}$alkyl, fluoro substituted C$_{1-6}$alkyl, fluoro substituted C$_{1-6}$alkoxy, aryl, heteroaryl, C$_{1-6}$alkoxy, —CN, —NO$_2$, —OH, —C(O)—O—C$_{1-6}$alkyl or —SiMe$_3$, wherein the aliphatic or aromatic portion of R$^a$ is further optionally substituted with from 1-3 R$^b$ groups, wherein each R$^b$ group is independently halogen, C$_{1-6}$alkyl, C$_{1-6}$alkoxy, —CN, —NO$_2$ or —OH.

In another embodiment of the method of preparing the compound of formula (Ia), the contacting of

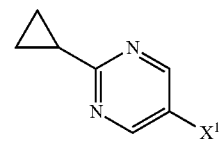

with formula (II) is carried out) in 2-methyltetrahydrofuran with nitrogen.

In another embodiment of the method of preparing the compound of formula (Ia), the method further comprises adding sodium bicarbonate and bis(triphenyl)palladium(II) dichloroide.

In another embodiment of the method of preparing the compound of formula (I), the contacting of formula L²-P¹ with formula (Ia) is carried out in dichloromethane and a solvent selected from the group consisting of pyridine, dichloromethane, THF, acetonitrile, toluene, dioxane, 2-methyl-THF, or a mixture thereof.

In another embodiment of the method of preparing the compound of formula (I), the contacting of formula L²-P¹ with formula (Ia) is carried out in dichloromethane and pyridine.

In another embodiment of the method of preparing the compound of formula (I), the contacting of formula L²-P¹ with formula (Ia) is carried out in dioxane and pyridine.

In another embodiment of the method of preparing the compound of formula (Ia), $X^1$ is Sn(Bu)₃.

In another embodiment of the method of preparing the compound of formula (Ia), $X^1$ is B(OR⁵)₂.

In another embodiment of the method of preparing the compound of formula (Ia), $X^1$ is B(OH)2.

In another embodiment of the method of preparing the compound of formula (Ia), $L^1$ is Br.

In another embodiment of the method of preparing the compound of formula (Ia), $P^2$ is 2,6-dichlorophenyl.

In another embodiment of the method of preparing the compound of formula (Ia), Q is F.

In another embodiment of the method of preparing the compound of formula (Ia), $L^1$ is Br, and $P^2$ is 2,6-dichlorophenyl; Q is F.

In yet another embodiment, the present disclosure provides a method for preparing a compound of formula (I):

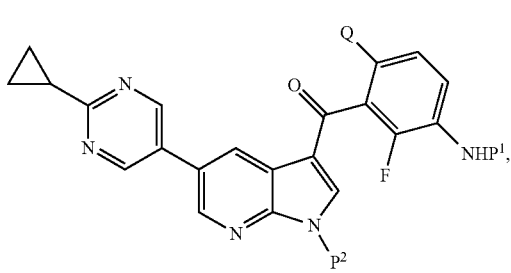

(I)

or a pharmaceutically acceptable salt, a solvate, a tautomer, an isomer or a deuterated analog thereof, said method comprising:
contacting a compound of formula (Ia) with L²-P¹ under conditions sufficient to form the compound of formula (I), wherein:
Q is F or H;
$P^2$ is —C(O)—R³ or —C(O)—OR⁴;
$P^1$ is

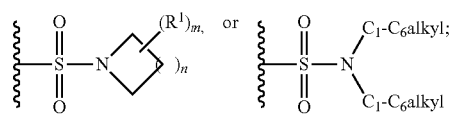

$R^1$ is H or halogen;
n is 0, 1 or 2;
m is 1 or 2;
$R^3$ is $C_{1-6}$alkyl, aryl, heteroaryl, aryl-$C_{1-2}$alkyl, heteroaryl-$C_{1-2}$alkyl, $C_{3-10}$cycloalkyl, $C_{3-10}$cycloalkyl-$C_{1-2}$alkyl, ethynyl or vinyl, each of which is optionally substituted with 1-3 $R^a$ groups;
$R^4$ is $C_{1-6}$alkyl, aryl, heteroaryl, aryl-$C_{1-2}$alkyl, heteroaryl-$C_{1-2}$alkyl, $C_{3-10}$cycloalkyl, $C_{3-10}$cycloalkyl-$C_{1-2}$alkyl, ethynyl or vinyl, each of which is optionally substituted with 1-3 $R^a$ groups; and
each $R^a$ group is independently halogen, $C_{1-6}$alkyl, fluoro substituted $C_{1-6}$alkyl, fluoro substituted $C_{1-6}$alkoxy, aryl, heteroaryl, $C_{1-6}$alkoxy, —CN, —NO₂, —OH, —C(O)—O—$C_{1-6}$alkyl, or —SiMe₃, wherein the aliphatic or aromatic portion of $R^a$ is further optionally substituted with from 1-3 $R^b$ groups, wherein each $R^b$ group is independently halogen, $C_{1-6}$alkyl, $C_{1-6}$alkoxy, —CN, —NO₂ or —OH.

In another embodiment of the method of preparing the compound of formula (I), the contacting of formula L²-P¹ with formula (Ia) is carried out in pyridine and a solvent selected from the group consisting of pyridine, dichloromethane, THF, acetonitrile, toluene, dioxane, 2-methyl-THF, or a mixture thereof.

In another embodiment of the method of preparing the compound of formula (I), the contacting of formula L²-P¹ with formula (Ia) is carried out in dichloromethane and pyridine.

In another embodiment of the method of preparing the compound of formula (I), the contacting of formula L²-P¹ with formula (Ia) is carried out in dioxane and pyridine.

In another embodiment of the method of preparing the compound of formula (I), the contacting of formula L²-P¹ with formula (Ia) is carried out in 1,4-dioxane and pyridine.

In another embodiment of the method of preparing the compound of formula (I), $L^1$ is Br.

In another embodiment of the method of preparing the compound of formula (I), $P^2$ is 2,6-dichlorophenyl.

In another embodiment of the method of preparing the compound of formula (I), $P^1$ is

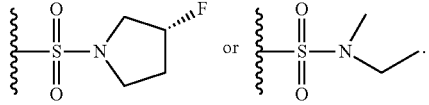

In another embodiment of the method of preparing the compound of formula (I), Q is F.

In another embodiment of the method of preparing the compound of formula (I), $P^1$ is

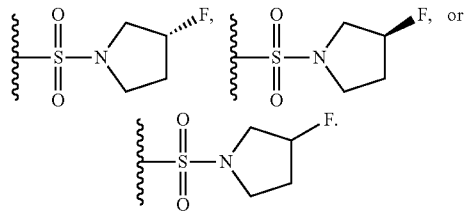

In another embodiment of the method of preparing the compound of formula (I), $P^1$ is

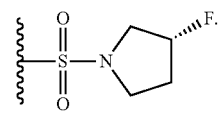 [SMILES: *S(=O)(=O)N1CC[C@@H](F)C1]

In another embodiment of the method of preparing the compound of formula (I), $P^1$ is

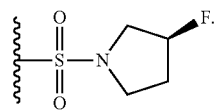 [SMILES: *S(=O)(=O)N1CC[C@H](F)C1]

In another embodiment of the method of preparing the compound of formula (I), P¹ is

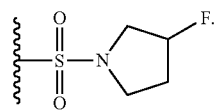 [SMILES: *S(=O)(=O)N1CCC(F)C1]

In another embodiment of the method of preparing the compound of formula (I), P¹ is

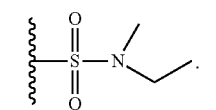 [SMILES: *S(=O)(=O)N(C)CC]

In another embodiment of the method of preparing the compound of formula (I), L¹ is Br, P² is 2,6-dichlorophenyl; and Q is F.

In another embodiment of the method of preparing the compound of formula (I), L¹ is Br, P² is 2,6-dichlorophenyl; Q is F, and P¹ is

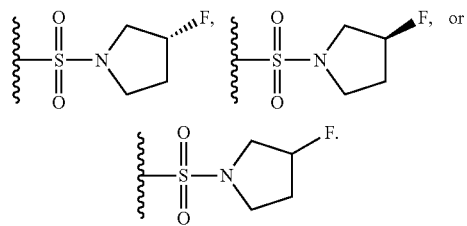

In another embodiment of the method of preparing the compound of formula (I), L¹ is Br, P² is 2,6-dichlorophenyl; Q is F, and P¹ is

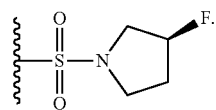 [SMILES: *S(=O)(=O)N1CC[C@H](F)C1]

In another embodiment of the method of preparing the compound of formula (I), L¹ is Br, P² is 2,6-dichlorophenyl; Q is F, and P¹ is

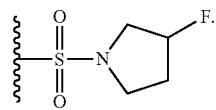 [SMILES: *S(=O)(=O)N1CCC(F)C1]

In another embodiment of the method of preparing the compound of formula (I), L¹ is Br, P² is 2,6-dichlorophenyl; Q is F, and P¹ is

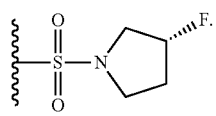 [SMILES: *S(=O)(=O)N1CC[C@@H](F)C1]

In another embodiment of the method of preparing the compound of formula (I), L¹ is Br, P² is 2,6-dichlorophenyl; Q is F, and P¹ is

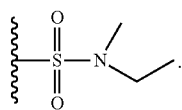 [SMILES: *S(=O)(=O)N(C)CC]

In yet another embodiment, the present disclosure provides a method for preparing a compound of formula (III):

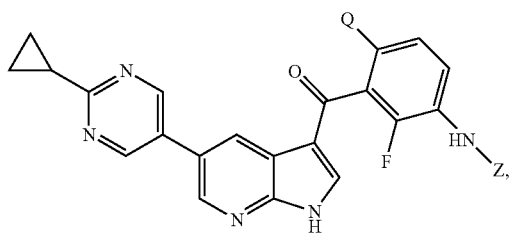

(III)

or a pharmaceutically acceptable salt, a solvate, a tautomer, an isomer or a deuterated analog thereof, said method comprising:

(1) reacting a compound of formula (Ib):

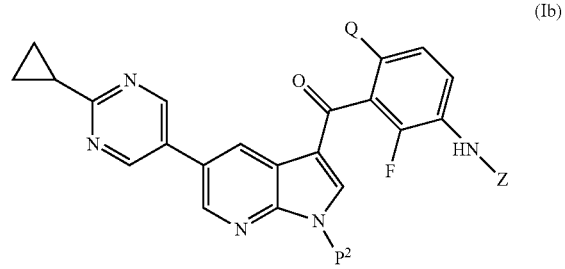

(Ib)

under conditions sufficient to N-deprotect formula (I) and form the compound of formula (III),
wherein:
Z is

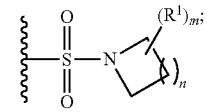

$R^1$ is fluoro or chloro;
Q is H or fluoro;
n is 0, 1 or 2;
m is 1 or 2;
$P^2$ is —C(O)—$R^3$ or —C(O)—$OR^4$;
$R^3$ is $C_{1-6}$alkyl, aryl, heteroaryl, aryl-$C_{1-2}$alkyl, heteroaryl-$C_{1-2}$alkyl, $C_{3-10}$cycloalkyl, $C_{3-10}$cycloalkyl-$C_{1-2}$alkyl, ethynyl or vinyl, each of which is optionally substituted with 1-3 substituents as described in this disclosure; and R⁴ is $C_{1-6}$alkyl, aryl, heteroaryl, aryl-$C_{1-2}$alkyl, heteroaryl-$C_{1-2}$alkyl, $C_{3-10}$cycloalkyl, $C_{3-10}$cycloalkyl-$C_{1-2}$alkyl, ethynyl or vinyl, each of which is optionally substituted with 1-3 substituents as described in this disclosure.

In another embodiment of the method for preparing a compound of formula (III):

R³ is $C_{1-6}$alkyl, aryl, heteroaryl, aryl-$C_{1-2}$alkyl, heteroaryl-$C_{1-2}$alkyl, $C_{3-10}$cycloalkyl, $C_{3-10}$cycloalkyl-$C_{1-2}$alkyl, ethynyl or vinyl, each of which is optionally substituted with 1-3 $R^a$ groups;

R⁴ is $C_{1-6}$alkyl, aryl, heteroaryl, aryl-$C_{1-2}$alkyl, heteroaryl-$C_{1-2}$alkyl, $C_{3-10}$cycloalkyl, $C_{3-10}$cycloalkyl-$C_{1-2}$alkyl, ethynyl or vinyl, each of which is optionally substituted with 1-3 $R^a$ groups; and each $R^a$ group is independently halogen, $C_{1-6}$alkyl, fluoro substituted $C_{1-6}$alkyl, fluoro substituted $C_{1-6}$alkoxy, aryl, heteroaryl, $C_{1-6}$alkoxy, —CN, —NO₂, —OH, —C(O)—O—$C_{1-6}$alkyl or —SiMe₃, wherein the aliphatic or aromatic portion of $R^a$ is further optionally substituted with from 1-3 $R^b$ groups, wherein each $R^b$ group is independently halogen, $C_{1-6}$alkyl, $C_{1-6}$alkoxy, —CN, —NO₂ or —OH.

In other embodiments of this disclosure, Z is

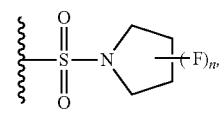

wherein n is 0, 1 or 2.

In other embodiments of this disclosure, Z is

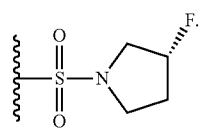

In other embodiments of the method of preparing a compound of formula (III), the compound of formula (III) is formula (IV):

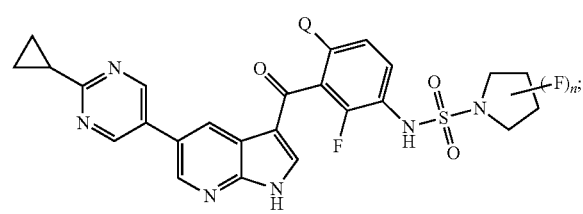

(IV)

and the compound of formula (Ib) is formula (Ic):

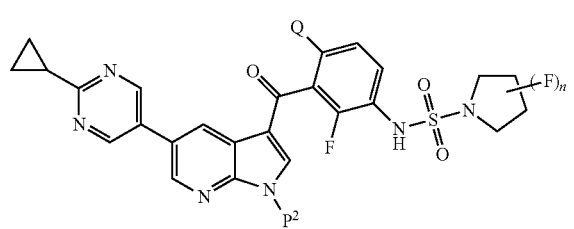

(Ic)

wherein:
Q is H or fluoro;
n is 0, 1 or 2;
P² is —C(O)—R³ or —C(O)—OR⁴;
R³ is $C_{1-6}$alkyl, aryl, heteroaryl, aryl-$C_{1-2}$alkyl, heteroaryl-$C_{1-2}$alkyl, $C_{3-10}$cycloalkyl, $C_{3-10}$cycloalkyl-$C_{1-2}$alkyl, ethynyl or vinyl, each of which is optionally substituted with 1-3 substituents as described in this disclosure; and
R⁴ is $C_{1-6}$alkyl, aryl, heteroaryl, aryl-$C_{1-2}$alkyl, heteroaryl-$C_{1-2}$alkyl, $C_{3-10}$cycloalkyl, $C_{3-10}$cycloalkyl-$C_{1-2}$alkyl, ethynyl or vinyl, each of which is optionally substituted with 1-3 substituents as described in this disclosure.

In another embodiment of the method for preparing a compound of formula (IV):

R³ is $C_{1-6}$alkyl, aryl, heteroaryl, aryl-$C_{1-2}$alkyl, heteroaryl-$C_{1-2}$alkyl, $C_{3-10}$cycloalkyl, $C_{3-10}$cycloalkyl-$C_{1-2}$alkyl, ethynyl or vinyl, each of which is optionally substituted with 1-3 $R^a$ groups;

R⁴ is $C_{1-6}$alkyl, aryl, heteroaryl, aryl-$C_{1-2}$alkyl, heteroaryl-$C_{1-2}$alkyl, $C_{3-10}$cycloalkyl, $C_{3-10}$cycloalkyl-$C_{1-2}$alkyl, ethynyl or vinyl, each of which is optionally substituted with 1-3 $R^a$ groups; and each $R^a$ group is independently halogen, $C_{1-6}$alkyl, fluoro substituted $C_{1-6}$alkyl, fluoro substituted $C_{1-6}$alkoxy, aryl, heteroaryl, $C_{1-6}$alkoxy, —CN, —NO₂, —OH, —C(O)—O—$C_{1-6}$alkyl or —SiMe₃, wherein the aliphatic or aromatic portion of $R^a$ is further optionally substituted with from 1-3 $R^b$ groups, wherein each $R^b$ group is independently halogen, $C_{1-6}$alkyl, $C_{1-6}$alkoxy, —CN, —NO₂, or —OH.

In another embodiment of the method of preparing the compound of formula (III) or (IIIb), formula (III) or (IIIb) is formula (IIIc):

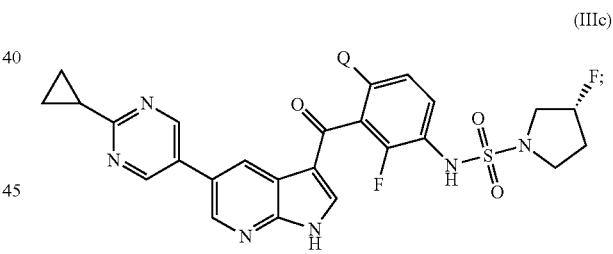

(IIIc)

and the compound of formula (Ib) or formula (Ic) is formula (Id):

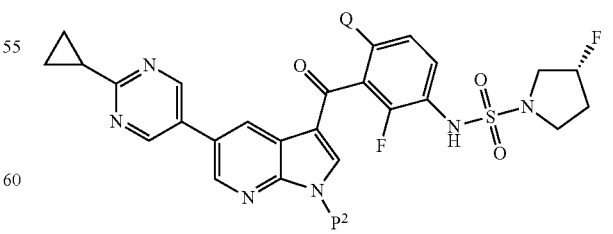

(Id)

wherein:
P² is —C(O)—R³ or —C(O)—OR⁴;
R³ is $C_{1-6}$alkyl, aryl, heteroaryl, aryl-$C_{1-2}$alkyl, heteroaryl-$C_{1-2}$alkyl, $C_{3-10}$cycloalkyl, $C_{3-10}$cycloalkyl- $C_{1-2}$alkyl, ethynyl or vinyl, each of which is optionally substituted with 1-3 substituents as described in this disclosure; and $R^4$ is $C_{1-6}$alkyl, aryl, heteroaryl, aryl-$C_{1-2}$alkyl, heteroaryl-$C_{1-2}$alkyl, $C_{3-10}$cycloalkyl, $C_{3-10}$cycloalkyl-$C_{1-2}$alkyl, ethynyl or vinyl, each of which is optionally substituted with 1-3 substituents as described in this disclosure.

In another embodiment of the method of preparing the compound of formula ((IIIc):

$R^3$ is $C_{1-6}$alkyl, aryl, heteroaryl, aryl-$C_{1-2}$alkyl, heteroaryl-$C_{1-2}$alkyl, $C_{3-10}$cycloalkyl, $C_{3-10}$cycloalkyl-$C_{1-2}$alkyl, ethynyl or vinyl, each of which is optionally substituted with 1-3 $R^a$ groups;

$R^4$ is $C_{1-6}$alkyl, aryl, heteroaryl, aryl-$C_{1-2}$alkyl, heteroaryl-$C_{1-2}$alkyl, $C_{3-10}$cycloalkyl, $C_{3-10}$cycloalkyl-$C_{1-2}$alkyl, ethynyl or vinyl, each of which is optionally substituted with 1-3 $R^a$ groups; and each $R^a$ group is independently halogen, $C_{1-6}$alkyl, fluoro substituted $C_{1-6}$alkyl, fluoro substituted $C_{1-6}$alkoxy, aryl, heteroaryl, $C_{1-6}$alkoxy, —CN, —NO$_2$, —OH, —C(O)—O—$C_{1-6}$alkyl or —SiMe$_3$, wherein the aliphatic or aromatic portion of $R^a$ is further optionally substituted with from 1-3 $R^b$ groups, wherein each $R^b$ group is independently halogen, $C_{1-6}$alkyl, $C_{1-6}$alkoxy, —CN, —NO$_2$, or —OH.

In another embodiment of the method of preparing the compound of formula (III), (IIIb) or (IIIc), $R^3$ or $R^4$ is phenyl optionally substituted with 1-3 $R^a$ groups, wherein each $R^a$ group is independently F, Cl, Br, I, —CH$_3$, —CH$_2$F, —CHF$_2$, —CF$_3$, t-butyl, —NO$_2$, —CN, —OCF$_3$, or —OH.

In another embodiment of the method of preparing the compound of formula (III), (IIIb) or (IIIc), $P^2$ is phenycarbonyl optionally substituted with 1-3 halogens.

In another embodiment of the method of preparing the compound of formula (III), (IIIb) or (IIIc), $P^2$ is 2,6-dichlorophenylcarbonyl.

In another embodiment of the method of preparing the compound of formula (III), $P^2$ is 2,6-dichlorophenylcarbonyl and Q is F.

In another embodiment of the method of preparing the compound of formula (III), the N-deprotection comprises adding ammonia in methanol.

In another embodiment of the method of preparing the compound of formula (III), formula (II) is first dissolved in tetrahydrofuran.

The agents B(OR$^5$)$_2$ (i.e., within the definition of $X^1$ of

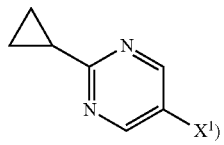

or is either commercially available or can be readily prepared in accordance with the procedures described in the literature. In some embodiments, —B(OR$^5$)$_2$ is:

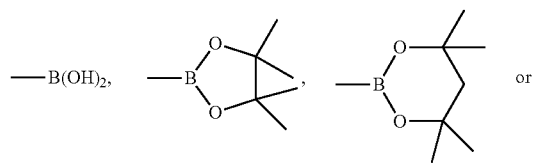

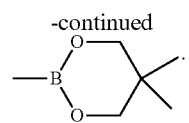

Various palladium or nickel complexes can be used for the preparation of compounds of formula (III). Preferably, palladium phosphine complexes are used in the reaction. The palladium complexes include, but are not limited to, Pd(PPh$_3$)$_4$, PdCl$_2$(PPh$_3$)$_2$, bis[1,2-bis(diphenylphosphino)ethane]palladium, bis(tri-t-butylphosphine)palladium, diacetobis(triphenylphosphine)palladium, tris(dibenzylideneacetone)dipalladium (Pd$_2$(dba)2), Pd(OAc)$_2$, dichloro[1,1'-bis(diphenylphosphino)ferrocene]palladium(II), and dichloro[1,1'-bis(di-i-propyl-phosphino)ferrocene]palladium (II). In one embodiment, the palladium complex is PdCl$_2$(PPh$_3$)$_2$. The palladium complexes can be present between 0.01 and 0.1 equivalents, e.g., about 0.01, 0.02, 0.025, 0.03, 0.04, 0.05, 0.06, 0.07, 0.08, 0.09 or 0.1 equivalents. Exemplary nickel complexes include, but are not limited to, NiCl$_2$ (dppf), bis(tricyclohexylphosphine) nickel(II) chloride (NiCl$_2$ (PCy$_3$)$_2$) and NiCl$_2$(PPh$_3$)$_2$.

The Suzuki coupling reaction can be carried out in various solvents, including, but not limiting to, toluene, dioxane, THF, 2-methyl-THF, water or a mixture thereof. In one embodiment, the reaction is carried out in dioxane or 2-methyl-THF. The reaction can be performed at a temperature between 50-100° C., 60-90° C. or 70-85° C. In one embodiment, the reaction is carried out using 0.025-0.05 eq of PdCl$_2$(PPh$_3$)$_2$, 2-3 eq of K$_2$CO$_3$ or NaHCO$_3$, 1 eq of compound of formula (I), 1.5-2 eq of compound of formula (IVb), 10 volumes of dioxane and 5 volumes of water.

The sulfonylation reaction described herein can be carried out in various solvents including, but not limiting to, pyridine, dichloromethane, THF, acetonitrile, toluene, dioxane, 2-methyl-THF or a mixture thereof. Excess solvents can be used during the reaction, for example, the solvents can be from 1-5 equivalents, such as 1, 1.5, 2, 2.5, 3, or 4 equivalents. The temperature for the reaction can be maintained from about 50-110° C., e.g., 50, 55, 60, 65, 70, 80, 85, 90, 95, 100, 105 or 110° C. In one embodiment, the reaction is carried out in a mixed solvents of pyridine and 10 volumes of dioxane at about 100° C.

The deprotection reaction can be conducted by reacting a compound of formula (IX) with NH$_3$ dissolved in an organic solvent at a temperature from about 50-110° C., e.g., 50, 55, 60, 65, 70, 80, 85, 90, 95, 100, 105 or 110° C. The solvents used include, but are not limited to, methanol (MeOH), ethanol (EtOH), dimethylformamide (DMF), dimethylacetamide (DMA), THF, dimethylsulfoxide (DMSO), dioxane, isopropanol (IPA) or combinations thereof. In one embodiment, the reaction can be conducted at 55° C. in the presence of NH$_3$ (5 eq), MeOH (5 eq, 10 volumes) and DMA (5 volumes). In another embodiment, the reaction can be conducted at 100° C. in the presence of THF (5 volumes) and NH$_3$/IPA (12 eq).

EXAMPLES

The following examples are offered to illustrate, but not to limit the claimed invention.

Certain molecules claimed in this disclosure can exist in different enantiomeric and diastereomeric forms and all such variants of these compounds are claimed.

Example 1: Preparation of (5-bromo-1H-pyrrolo[2,3-b]pyridin-3-yl)-(2,6-difluoro-3-nitrophenyl)methanone (3)

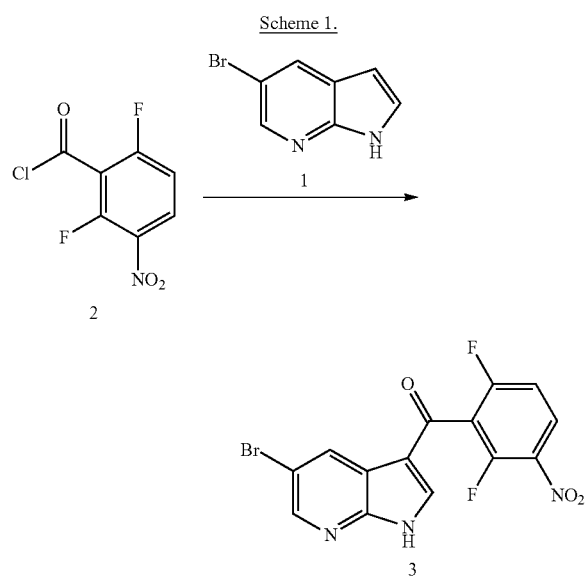

To an 50-liter flask was added 1,2-dichloroethane (DCE, 20 L), followed by 5-bromoazaindole (1) (2 kg, 10.152 mol) to result an orange slurry. Aluminum Chloride (5.421 kg, 40.608 mol) was slowly added to the flask. The first 1.5 kg of the addition was exothermic resulting a dark solution. The rest of the AlCl$_3$ was added to give a reaction mixture. To the reaction mixture was added 2,6-difluoro-3-nitrobenzoyl chloride 2 (2.25 kg, 10.125 mol) via an addition funnel over a period of 1.5 h. During the addition, the reaction temperature was maintained at or below 45° C. After the addition, the reaction mixture was stirred at 50° C. overnight, cooled to room temperature (~22° C.) and transferred into two separate 20 L flasks. Water (25 L) and acetonitrile (12 L) were added to a 50-liter flask and cooled to 0° C. The reaction mixture was quenched by adding water/acetonitrile solution while keeping the temperature at or below 40° C. The mixture obtained was filtered, and the filtrate was washed with acetonitrile:water (1:1, 2×4 L), water (4 L) and acetonitrile (4 L), followed by drying in vacuum. Compound 3 (2.948 kg, 73.4% yield) was obtained. MS (ESI): M+H$^+$=382.9 and 383.9. $^1$H NMR (DMSO-d$_6$, δ ppm): 7.55 (1H, m), 8.47 (2H, m), 8.53 (1H, d, J=2.2 Hz), 8.65 (1H, d, J=2.2 Hz), 13.25 (1H, s).

Example 2: Preparation of (3-amino-2,6-difluorophenyl)-(5-bromo-1H-pyrrolo[2,3-b]pyridin-3-yl)methanone (4)

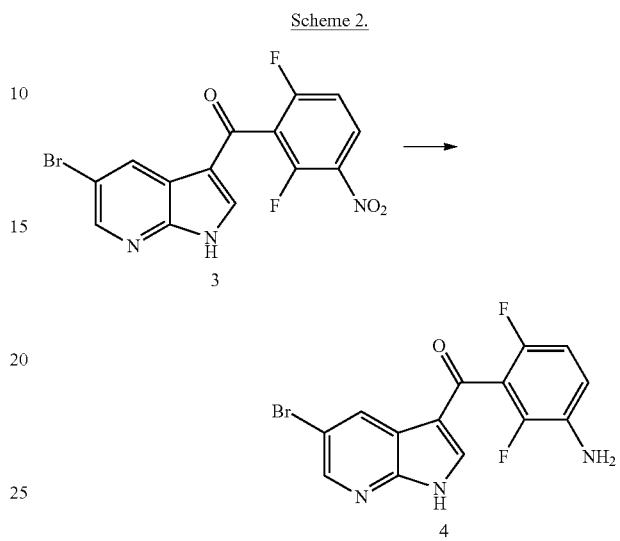

A 50-liter flask was added 2-methyl-tetrahydrofuran (2-methyl-THF) (36 L), compound 3 (2.85 kg, 7.455 mol) and tin(II) chloride (5.03 kg, 22.365 mol). The mixture was heated to 60° C. Upon completion, the reaction was quenched with an aqueous potassium carbonate solution (20%). The resulting mixture was filtered with celite and the solid residue was washed with 2-methyl-THF and tetrahydrofuran (THF). The filtrate was washed with an aqueous NaCl solution (15 L, 10%) and the organic layer was separated. The organic layer was further washed with an aqueous NaCl solution (15 L, 20%) and concentrated on a rotovap to yield compound 4 (2.536 kg, 96.65% yield). MS (ESI): M+H$^+$=353 and 354. $^1$H NMR (DMSO-d$_6$, δ ppm): 5.22 (2H, s), 6.93 (2H, m), 8.12 (1H, s), 8.47 (1H, d J=2.3 Hz), 8.54 (1H, d J=1.6 Hz), 13.2 (1H, s).

Example 3: Preparation of (3-amino-2,6-difluorophenyl)-[5-bromo-1-(2,6-dichlorobenzoyl)pyrrolo[2,3-b]pyridin-3-yl]methanone (5)

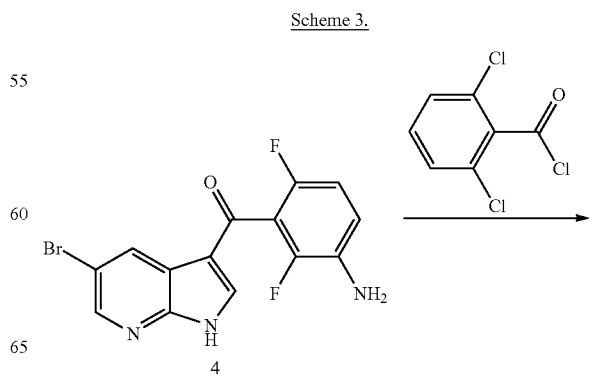

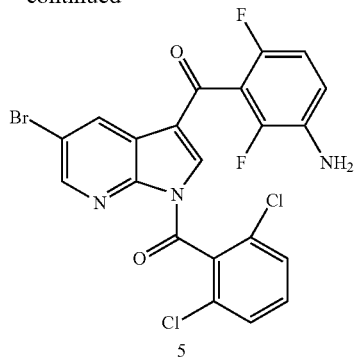

Compound 4 (2.5 kg, 7.114 mol) obtained from Example 2 was added into a 50-liter flask and cooled to 9.3° C. To compound 4 in the 50-liter flask was added triethylamine (0.864 kg, 8.537 mol), followed by 4-dimethylaminopyridine (DMAP) (0.087 kg, 0.7114 mol) and 2,6-dichlorobenzoyl chloride (1.34 kg, 6.40 mol) in 2-methyl-THF (25 L) over a period of 2 hrs. The reaction was quenched with methanol (0.30 L at room temperature and added an aqueous NaCl solution (12.5 L, 15%) and celite (0.5 kg). The mixture was stirred and filtered through celite. The filtrate was concentrated and added 5 volumes of heptanes. The resulting solution was stirred for about 1 hr and dried with sodium sulfate (1 kg) and filtered. Compound 5 was isolated by removing the solvents under vacuum (3.47 kg, 92.93% yield). MS (ESI): M+H$^+$=524, 525.8, 527.8. $^1$H NMR (DMSO-d$_6$, δ ppm): 5.36 (2H, s), 7.01 (2H, m), 7.68 (3H, s), 8.34 (1H, brs), 8.61 (1H, brs), 8.72 (1H, d J=2.3 Hz).

Example 4: Preparation of (3-(3-amino-2,6-difluorobenzoyl)-5-(2-cyclopropylpyrimidin-5-yl)-1H-pyrrolo[2,3-b]pyridin-1-yl)(2,6-dichlorophenyl)methanone

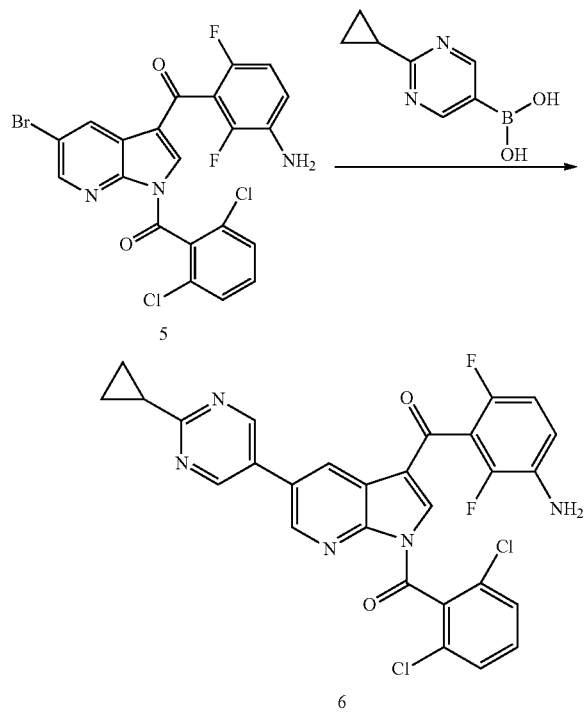

Compound 5 (40 g, 0.076 moles) and 2-cyclopropylpyrimidin-5-yl-5-boronic acid (Compound A) (23 g, 0.141 moles) in 2 methyltetrahydrofuran (2-MeTHF) (1,720 mL) which 8% sodium bicarbonate (sparged with nitrogen) and bis(triphenylphosphine)palladium(II) dichloride (1 g, 0.0014 moles) were added. The mixture was heated to reflux to give Compound 6 which was isolated, washed and dried. (27.4 g, 64% yield). LCMS: m/z=564.0 (M+H)$^+$. $^1$H NMR (DMSO-d6, δ ppm): 9.05 (s, 2H), 9.00 (s, 1H), 8.62 (s, 1H), 8.58 (s, 1H), 7.70 (m, 3H), 7.04 (m, 2H), 5.36 (br s, 2H), 2.30 (m, 1H), 1.16 (m, 4H).

Example 5: Preparation of (R)—N-(3-(5-(2-cyclopropylpyrimidin-5-yl)-1-(2,6-dichlorobenzoyl)-1H-pyrrolo[2,3-b]pyridine-3-carbonyl)-2,4-difluorophenyl)-3-fluoropyrrolidine-1-sulfonamide

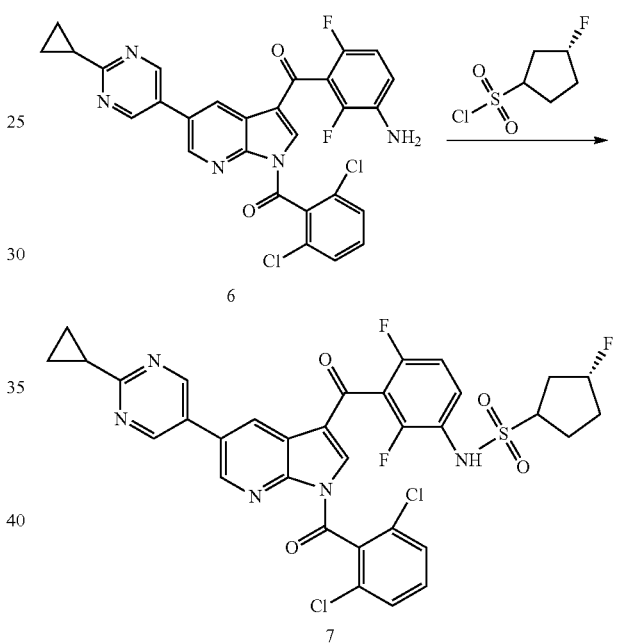

Compound 6 (15 g, 021 moles), 1,4 dioxane (150 ml), pyridine (15 ml, 49.6 moles), and Compound B (3-R-fluropyrrolidine sulfonyl chloride, 11.81 g, 0.063 moles) were charged to a flask. The reaction was stirred at room temperature and then heated to 50° C. and allowed to react overnight. Then charged to the reaction flask were ethyl acetate (60 ml) and water (60 ml). The organic layer was separated, washed, treated with activated carbon (Darco KG-B, 2.25 g) and filtered through a celite pad to yield Compound 7 (10 g, 67% yeld). $^1$H NMR (DMSO-d6, δ ppm): 9.70 (s, 1H), 9.02 (s, 2H), 8.81 (m, 2H), 8.57 (m, 2H), 7.71 (m, 2H), 7.38 (m, 2H), 5.24-5.37 (2s, 1H), 3.31-3.42 (m, 4H), 2.05-2.29 (m, 3H), 1.12 (m, 4H).

Compound B was obtained by combining commercially available 3-R-fluoropyrrolidine HCl salt (20 kg, 159.3 moles) and commercially available sulfuryl chloride (21 kg, 155.6 moles) in a solution of dichloromethane (293 kg) and trimethylamine (32 kg) to yield (R)-3 Fluoropyrrolidine dulfonyl chloride (Compound B, 23 kg, 77% yield).

Example 6: Preparation of (R)—N-(3-(5-(2-cyclo-propylpyrimidin-5-yl)-1H-pyrrolo[2,3-b]pyridine-3-carbonyl)-2,4-difluorophenyl)-3-fluoropyrrolidine-1-sulfonamide

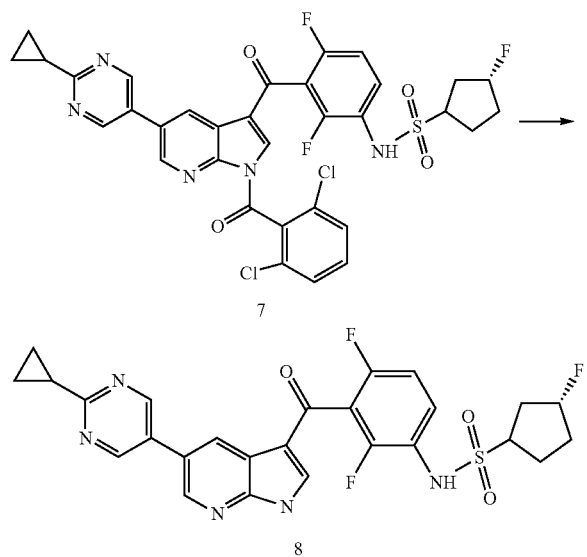

Compound 7 (26.9 kg) was dissolved in tetrahydrofuran (95.8 kg) and 7N ammonia in methanol (50.2 kg) was added to the reaction mixture. Once the reaction was deemed complete by HPLC, Compound 8 was isolated by solvent exchange with dichloromethane. Compound 8 was dissolved in tetrahydrofuran, filtered and concentrated, and the isolated material was purified, isolated and triturated in WFI (Water for Injection) (17.8 kg, 87% yield).

All patents, patent applications and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present disclosure is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

While this invention has been disclosed with reference to specific embodiments, it is apparent that other embodiments and variations of this invention may be devised by others skilled in the art without departing from the true spirit and scope of the invention.

The disclosure illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. Thus, for an embodiment of the disclosure using one of the terms, the disclosure also includes another embodiment wherein one of these terms is replaced with another of these terms. In each embodiment, the terms have their established meaning. Thus, for example, one embodiment may encompass a method "comprising" a series of steps, another embodiment would encompass a method "consisting essentially of" the same steps, and a third embodiment would encompass a method "consisting of" the same steps. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended claims.

In addition, where features or embodiments of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any two different values as the endpoints of a range. Such ranges are also within the scope of the described invention.

Thus, additional embodiments are within the scope of the disclosure and within the following claims.

What is claimed is:

1. A method for preparing a compound of formula (I):

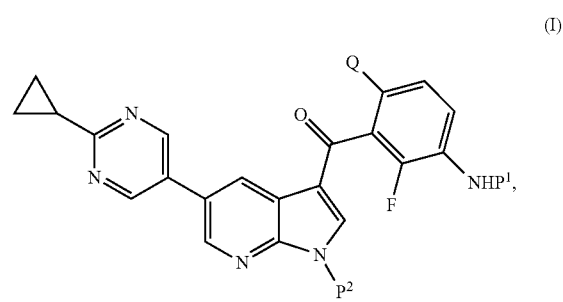

or a pharmaceutically acceptable salt, a solvate or a tautomer thereof, said method comprising:
contacting a compound of formula (Ia):

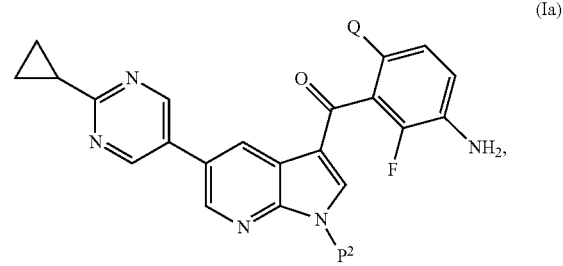

with $L^2$-$P^1$ under conditions sufficient to form the compound of formula (I), wherein:

Q is F or H;
P² is —C(O)—R³ or —C(O)—OR⁴;
P¹ is

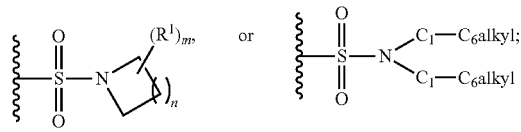

R¹ is H or halogen;
n is 0, 1 or 2;
m is 1 or 2;
R³ is $C_{1-6}$alkyl, aryl, heteroaryl, aryl-$C_{1-2}$alkyl, heteroaryl-$C_{1-2}$alkyl, $C_{3-10}$cycloalkyl, $C_{3-10}$cycloalkyl-$C_{1-2}$alkyl, ethynyl or vinyl, each of which is optionally substituted with 1-3 $R^a$ groups;
R⁴ is $C_{1-6}$alkyl, aryl, heteroaryl, aryl-$C_{1-2}$alkyl, heteroaryl-$C_{1-2}$alkyl, $C_{3-10}$cycloalkyl, $C_{3-10}$cycloalkyl-$C_{1-2}$alkyl, ethynyl or vinyl, each of which is optionally substituted with 1-3 $R^a$ groups;
L² is Br, Cl, I, tosyl-O—, mesyl-O—, trifluoromethanesulfonyl-O—, —C(O)—O—CF₃ or —C(O)—O—CH₃; and
each $R^a$ group is independently halogen, $C_{1-6}$alkyl, fluoro substituted $C_{1-6}$alkyl, fluoro substituted $C_{1-6}$alkoxy, aryl, heteroaryl, $C_{1-6}$alkoxy, —CN, —NO₂, —OH, —C(O)—O—$C_{1-6}$alkyl, or —SiMe₃, wherein the aliphatic or aromatic portion of $R^a$ is further optionally substituted with from 1-3 $R^b$ groups, wherein each $R^b$ group is independently halogen, $C_{1-6}$alkyl, $C_{1-6}$alkoxy, —CN, —NO₂ or —OH.

2. The method of claim 1, wherein the contacting of L²-P¹ with the compound of formula (Ia) is carried out in pyridine and a solvent selected from the group consisting of dichloromethane, tetrahydrofuran, acetonitrile, toluene, dioxane, 2-methyl-tetrahydrofuran, and a mixture thereof.

3. The method of claim 1, wherein L² is Br.

4. The method of claim 3, wherein P² is —C(O)—R³ and R³ is 2,6-dichlorophenyl.

5. The method of claim 4, wherein Q is F.

6. The method of claim 5, wherein P¹ is:

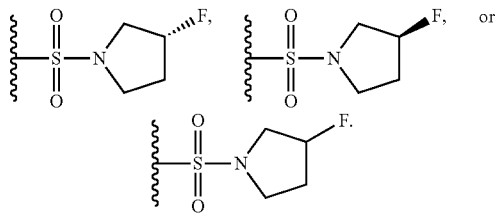

7. The method of claim 1, wherein L² is Br, P² is —C(O)—R³, R³ is 2,6-dichlorophenyl, Q is F, and P¹ is

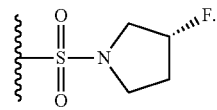

* * * * *

UNITED STATES PATENT AND TRADEMARK OFFICE
CERTIFICATE OF CORRECTION

PATENT NO. : 9,994,567 B2
APPLICATION NO. : 15/705097
DATED : June 12, 2018
INVENTOR(S) : Prabha N. Ibrahim et al.

Page 1 of 2

It is certified that error appears in the above-identified patent and that said Letters Patent is hereby corrected as shown below:

In the Specification

At Column 30, Lines 21-45, please replace the following chemical structures and text:

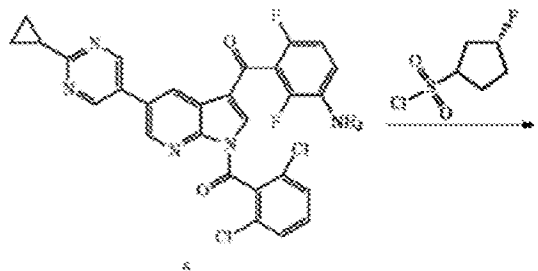

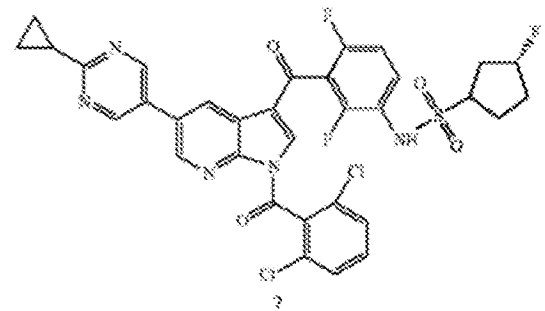

"     ?     "

With:

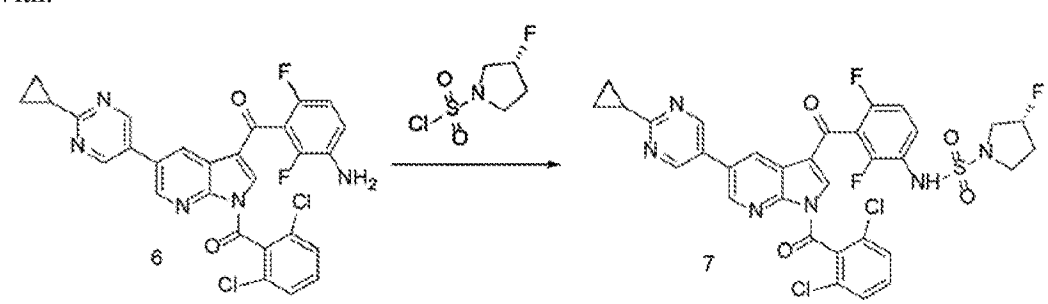

--                                                              --

Signed and Sealed this
Ninth Day of July, 2019

Andrei Iancu
*Director of the United States Patent and Trademark Office*

CERTIFICATE OF CORRECTION (continued)  
U.S. Pat. No. 9,994,567 B2

Page 2 of 2

At Column 31, Lines 7-28, please replace the following chemical structures and text:

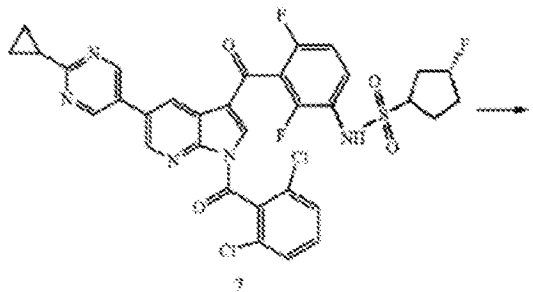

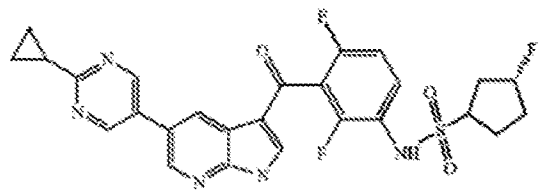

" 8 "

With:

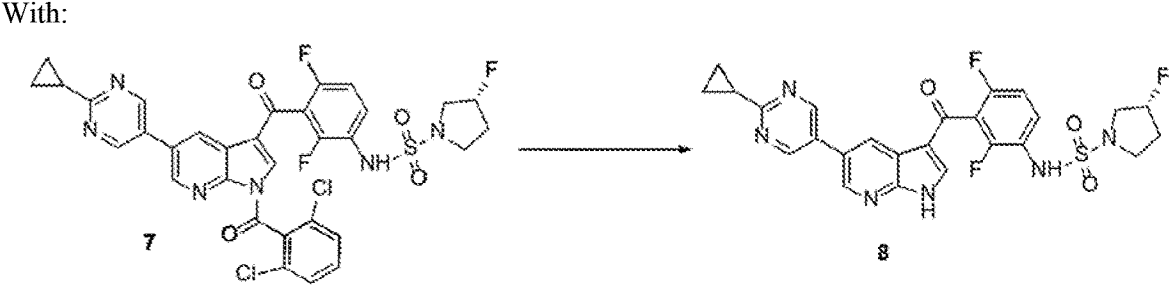

-- --